(12) United States Patent
Niwa et al.

(10) Patent No.: US 7,662,612 B2
(45) Date of Patent: Feb. 16, 2010

(54) CHEMICAL SENSOR DEVICE

(75) Inventors: Kazuhiro Niwa, Kasugai (JP); Masashi Nishiguchi, Kasugai (JP); Toru Onouchi, Ena-gun (JP)

(73) Assignee: Panasonic Corporation, Aichi (JP)

( * ) Notice: Subject to any disclaimer, the term of this patent is extended or adjusted under 35 U.S.C. 154(b) by 340 days.

(21) Appl. No.: 10/275,783

(22) PCT Filed: May 10, 2001

(86) PCT No.: PCT/JP01/03917

§ 371 (c)(1),
(2), (4) Date: Nov. 8, 2002

(87) PCT Pub. No.: WO01/86275

PCT Pub. Date: Nov. 15, 2001

(65) Prior Publication Data
US 2003/0180184 A1    Sep. 25, 2003

(30) Foreign Application Priority Data
May 11, 2000    (JP)    ............... 2000-138671
Jul. 25, 2000    (JP)    ............... 2000-223406

(51) Int. Cl.
C12M 3/00    (2006.01)

(52) U.S. Cl. .................................. 435/287.2

(58) Field of Classification Search ............ 204/164, 204/193, 403.1–403.6, 601; 356/244, 300–3, 356/311, 319, 326; 422/100, 50–73; 435/4–7.95, 435/800, 804–810, 290, 283.1, 285.2–289.1, 435/973, 290.1; 436/514–547, 73, 74, 800, 436/149
See application file for complete search history.

(56) References Cited

U.S. PATENT DOCUMENTS

| 4,975,175 | A | * | 12/1990 | Karube et al. | .......... 204/403.12 |
| 5,063,081 | A | * | 11/1991 | Cozzette et al. | ................ 435/4 |
| 5,571,568 | A | * | 11/1996 | Ribi et al. | .................... 427/487 |
| 5,759,364 | A | * | 6/1998 | Charlton et al. | ........ 204/403.14 |
| 5,805,048 | A | | 9/1998 | Saitoh et al. | |
| 5,830,680 | A | * | 11/1998 | Meyerhoff et al. | ......... 435/7.92 |
| 5,837,454 | A | | 11/1998 | Cozzette et al. | |
| 5,846,392 | A | * | 12/1998 | Knoll | ......................... 205/778 |
| 5,856,203 | A | * | 1/1999 | Robinson et al. | ............ 436/518 |
| 6,020,207 | A | * | 2/2000 | Liu | ............................ 436/164 |
| 6,245,296 | B1 | * | 6/2001 | Ligler et al. | ................... 422/57 |
| 6,254,830 | B1 | * | 7/2001 | Pivarnik et al. | .......... 422/82.07 |
| 6,320,295 | B1 | * | 11/2001 | McGill et al. | ............ 310/313 R |
| 6,322,963 | B1 | * | 11/2001 | Bauer | .............................. 435/4 |
| 6,387,707 | B1 | * | 5/2002 | Seul et al. | .................... 436/164 |
| 6,388,788 | B1 | * | 5/2002 | Harris et al. | ................. 359/196 |
| 6,416,642 | B1 | * | 7/2002 | Alajoki et al. | .............. 204/451 |
| 6,478,938 | B1 | * | 11/2002 | Paek et al. | ............. 204/403.01 |
| 6,548,311 | B1 | * | 4/2003 | Knoll | .......................... 436/524 |
| 6,602,714 | B1 | * | 8/2003 | Tagge et al. | ..................... 436/2 |
| 6,780,591 | B2 | * | 8/2004 | Williams et al. | ............... 435/6 |
| 6,803,238 | B1 | * | 10/2004 | Eggers | ........................ 436/518 |
| 6,846,654 | B1 | * | 1/2005 | Blackburn et al. | ........... 435/7.1 |
| 2001/0053529 | A1 | * | 12/2001 | Gindilis | ...................... 435/7.1 |

FOREIGN PATENT DOCUMENTS

JP        08-16388 A      6/1996
WO    WO 87/03093 A1    5/1987

OTHER PUBLICATIONS

Hansen, "Principles and Applications of Flow Injection Analysis in Biosensor", Journal of Molecular Recognition, vol. 9, 316-325 (1996).*

* cited by examiner

*Primary Examiner*—Ann Y Lam
(74) *Attorney, Agent, or Firm*—Snell & Wilmer L.L.P.

(57) ABSTRACT

A sensor device is provided for performing rapid and high-sensitivity detection. The sensor device comprising at least one support for immobilizing a subject to be detected and a cell for containing a solution in which a reaction product generated from the subject to be detected is diffused. At least one reaction region having a constant concentration of the reaction product is formed by diffusion of the reaction product into the solution, and the reaction region is formed in such a manner that the reaction product is specifically detected in a predetermined measurement time.

21 Claims, 22 Drawing Sheets

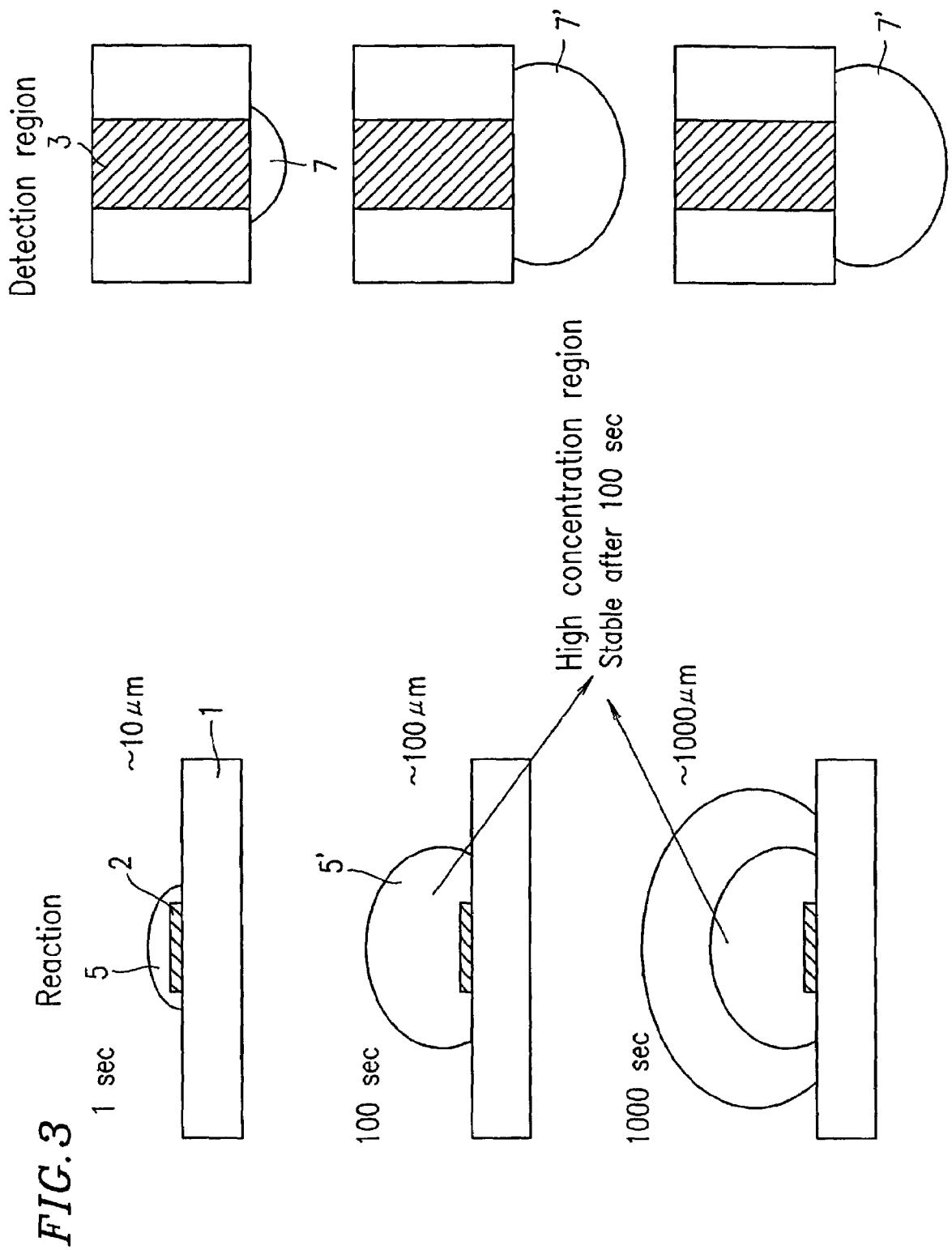

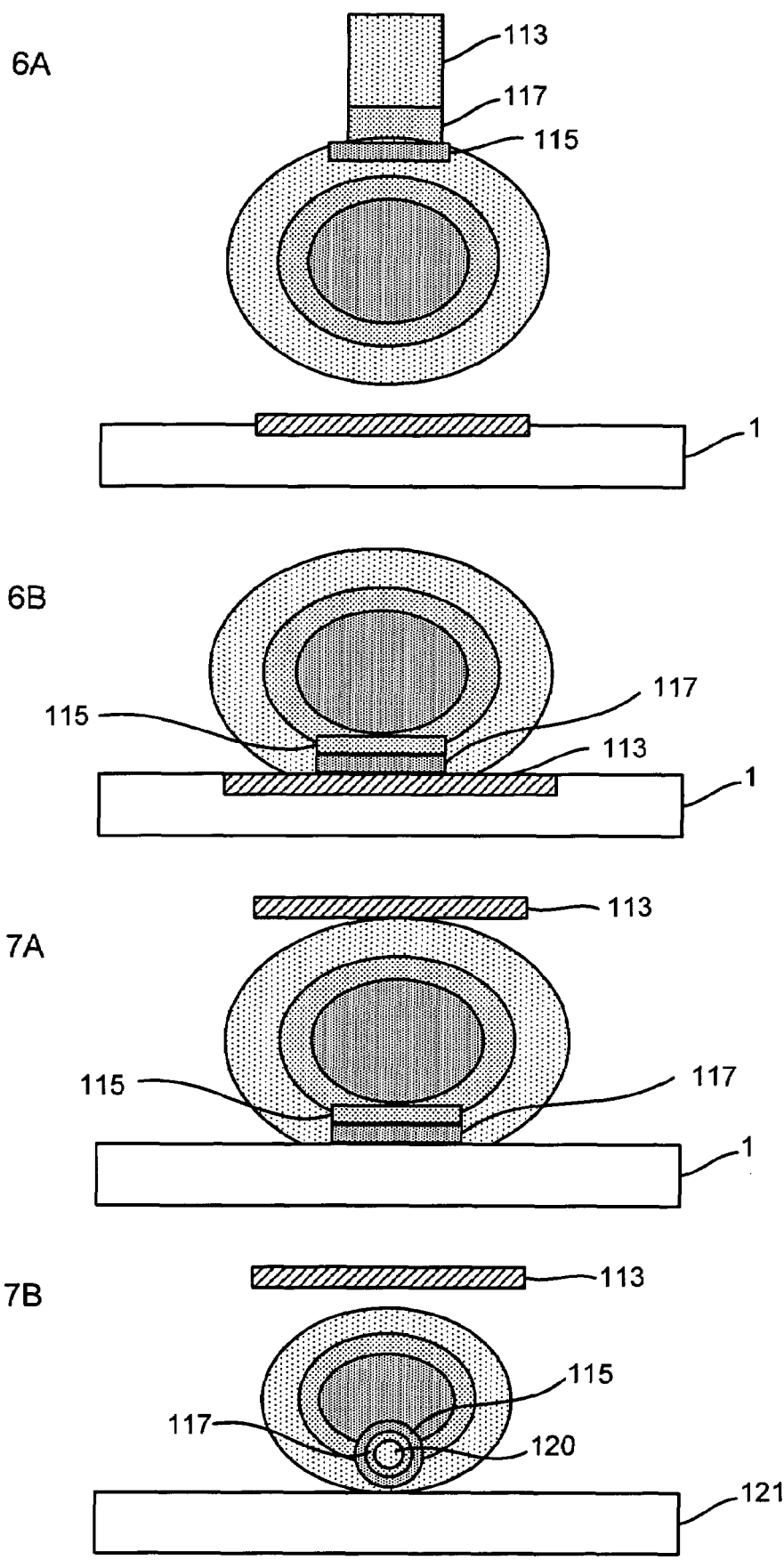

FIG.8
FIG.9
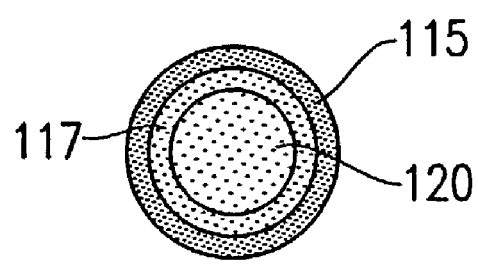
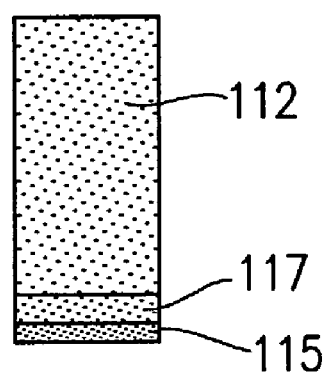

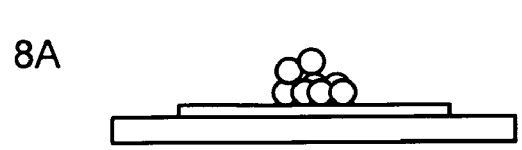
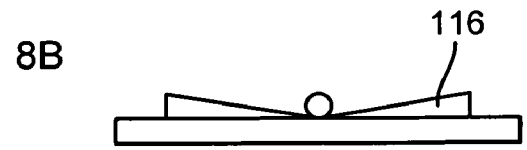
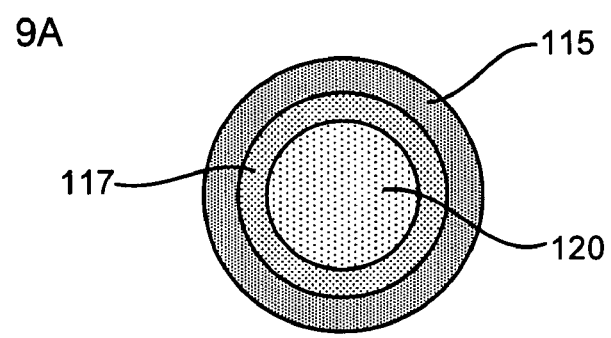
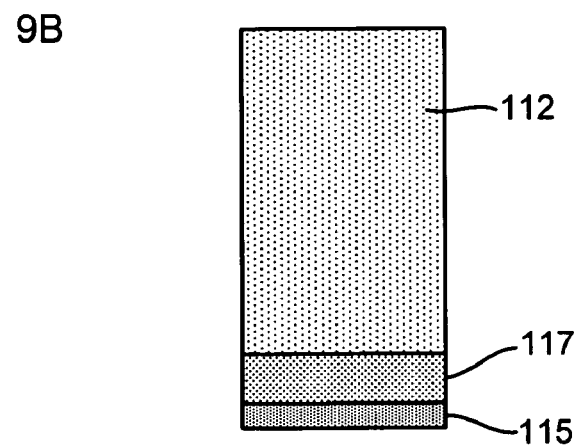

FIG. 13
(a) 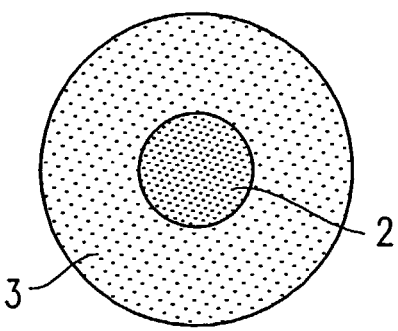
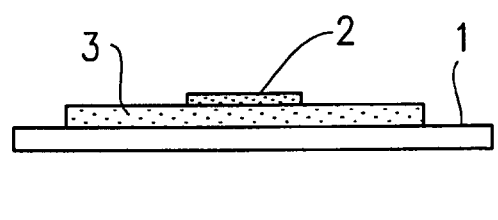
(b) 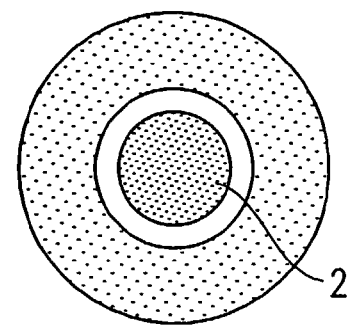
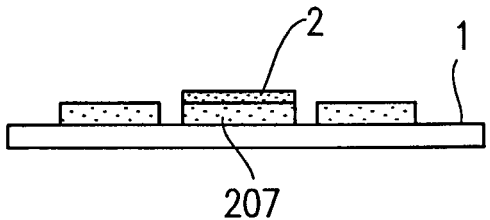
(c) 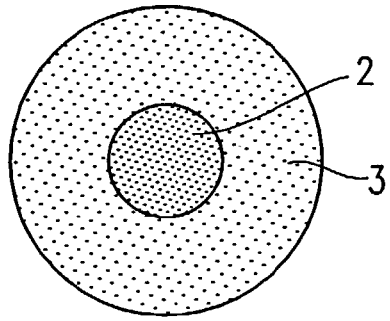
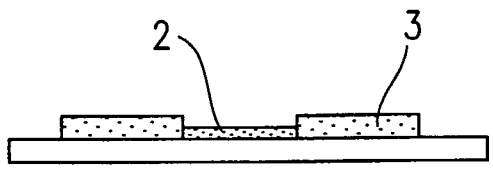

FIG.14
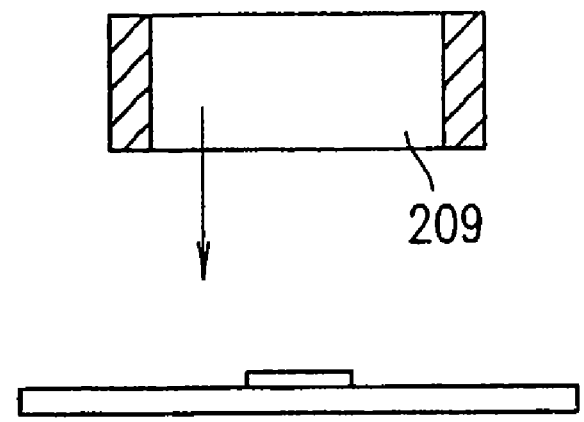
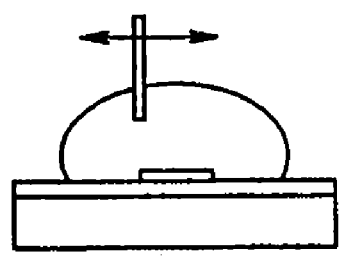
FIG. 15A
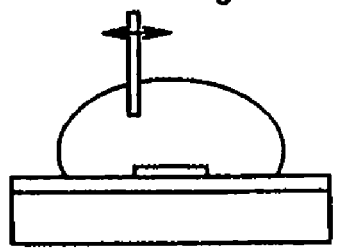
FIG. 15B
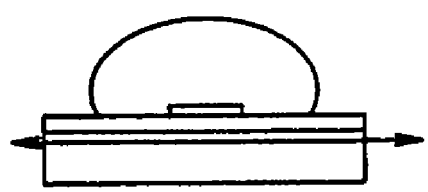
FIG. 15C

FIG.16
Loading and unloading solution
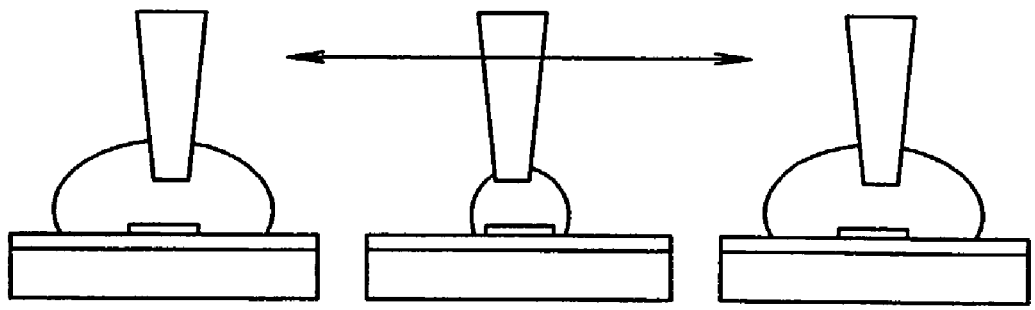
Exchanging solution
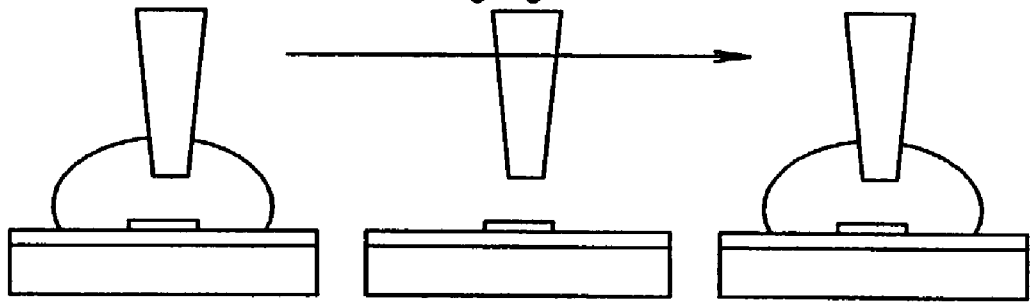
Continue supplying solution
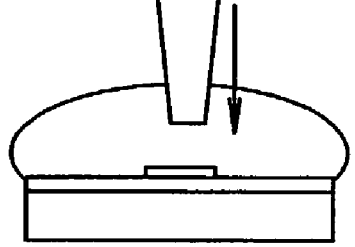
Allowing solution to flow
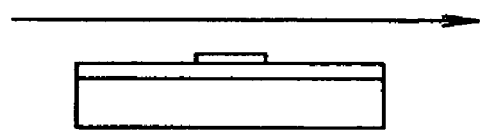

FIG. 17

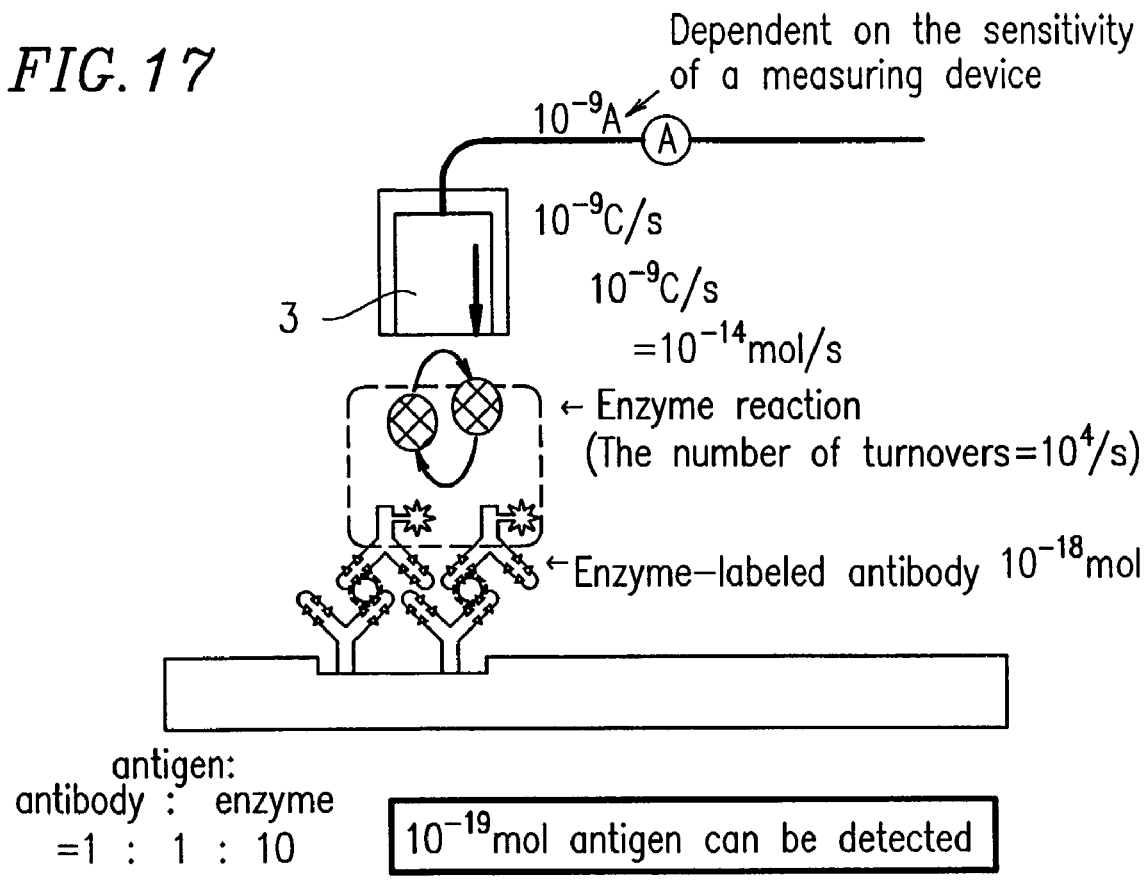

Dependent on the sensitivity of a measuring device
$10^{-9}A$
$10^{-9}C/s$
$10^{-9}C/s = 10^{-14}$ mol/s
← Enzyme reaction (The number of turnovers=$10^4$/s)
←Enzyme-labeled antibody $10^{-18}$ mol antigen: antibody : enzyme = 1 : 1 : 10

$10^{-19}$ mol antigen can be detected

Measurement aqueous solution (FMA solution)
Ferrocene methanol (FMA)    0.5mM
Hydrogen peroxide ($H_2O_2$)    5mM
Potassium chloride (KCl)    0.1M
Disodium hydrogen phosphate ($Na_2HPO_4$)    0.1M
pH=7.8

Enzyme/electrode reaction

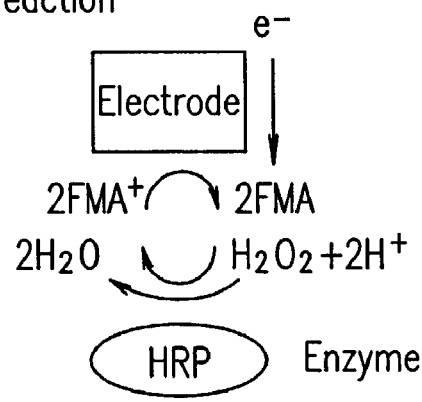

HRP    Enzyme (a) Radius :50μm Antibody-immobilized region on the substrate
Radius :250μm (b) Radius :50μm Antibody-immobilized region on the electrode
Radius :250μm
Unit : μm

US 7,662,612 B2

CHEMICAL SENSOR DEVICE

TECHNICAL FIELD

The present invention relates to a sensor device for detecting rapidly and specifically a very small amount of an analyte, such as a chemical substance, a protein, a microorganism, a virus, or the like, and a detection method using the same.

BACKGROUND ART

As a conventional sensor device for detecting a very small amount of an analyte, an enzyme electrode immunosensor is known. The sensor uses an immobilized antibody, a labeled antibody to which an enzyme is linked, and an electrode, to detect an analyte, which is linked to the immobilized antibody, where the labeled antibody linked to the analyte is a subject to be detected. The amount of the analyte is detected as a change in the current produced by oxidation and reduction of a product by an enzyme reaction using the electrode. FIG. 2 shows a conventional enzyme electrode immunosensor. As shown in FIG. 2, in the conventional enzyme electrode immunosensor, antibodies 102 are immobilized on the entirety of a bottom surface of a detection cell 101. Analyte molecules (antigens) 103 in a specimen are diffused in a solution within the cell, and reach and specifically bind to the immobilized antibodies 102. A labeled antibody 105 linked to an enzyme 104 is allowed to bind additionally to the analyte 103, resulting in formation of a sandwich complex. Excess antigens and labeled antibodies are washed out before adding a reaction solution 106 containing a substrate 107 for an enzyme reaction. The substrate 107 is converted to an enzyme reaction product 108 by action of the enzyme. The enzyme reaction product 108 is further subjected to oxidation and reduction by an electrode 3, thereby detecting the analyte.

The potential of the electrode needs to be held at a predetermined potential for the purpose of electrochemical oxidation and reduction of the enzyme reaction product 108 (not shown in FIG. 2). Therefore, the potential of the electrode for oxidation and reduction is set to be a potential based on the potential of a reference electrode placed in the reaction solution as a reference potential.

Although such a conventional enzyme electrode immunosensor device advantageously has a relatively simple structure, detection rate and detection sensitivity may not be obtained to sufficient extent in a practical sense for some subjects to be detected. Some sensor devices employ a labeled antibody labeled with a fluorescent dye instead of an enzyme. Unfortunately, detection of fluorescence complicates the procedure. The present invention is provided to solve the problems of the above-described conventional sensor devices. The object of the present invention is to eliminate the above-described problems.

the potential of the electrode for oxidation and reduction is set to be the potential of a reference electrode placed in the reaction solution as a reference potential

DISCLOSURE OF THE INVENTION

Although such a conventional enzyme electrode immunosensor advantageously has a relatively simple device structure, a detection rate and a detection sensitivity cannot be obtained to sufficient extent in a practical sense, depending on the subject to be detected. Some sensor device employs a labeled antibody labeled with a fluorescent dye instead of an enzyme. Unfortunately, detection of fluorescence causes the procedure to be complicated. The present invention is provided to solve the problems of the above-described conventional sensor devices. The object of the present invention is to eliminate the above-described problems.

The present invention relates to a sensor device, comprising at least one support for fixing a subject to be detected, and a cell for containing a solution in which a reaction product generated from the subject to be detected is diffused. At least one reaction region having a constant concentration of the reaction product is formed by diffusion of the reaction product into the solution, and the reaction region is formed in such a manner that the reaction product is specifically detected in a predetermined measurement time.

Preferably, the sensor device comprises a plurality of reaction regions. The plurality of reaction regions may be separately formed by different reaction products.

Preferably, the sensor device may further comprise detection means.

The subject to be detected may be immobilized by fixing means.

The detection means may have a detection region, and the detection region may include the reaction region.

Alternatively, the detection means may have a detection region, and the detection region may overlap the reaction region.

Alternatively, the detection means may have a detection region, and the detection region may be included in the reaction region.

Preferably, the support may be a particular region on a base plate.

Alternatively, the support may be a particulate or a rod-shaped member.

Preferably, the measurement time may be 30 minutes, more preferably 10 minutes, even more preferably 5 minutes, still more preferably 3 minutes, and most preferably 1 minute.

The detection means may measure light or heat.

Preferably, the detection means may comprise at least one electrode.

Preferably, the electrode may act on the reaction product and generate an electrical signal corresponding to the amount of the reaction product.

The subject to be detected may be an enzyme, and the reaction product may be an enzyme reaction product.

The subject to be detected may be an antibody or an enzyme linked to a peptide.

The fixing means may be an antigen or an antigen-antibody complex.

In one embodiment, the subject to be detected may be an enzyme linked to a first antibody linked to an antigen, and the fixing means may be a second antibody.

Preferably, the subject to be detected may be immobilized in a region having a diameter of several tens to several hundreds of μm, and the detection means may be an electrode having a diameter of 1 mm or less.

In one embodiment, when the subject to be detected is measured, the electrode may approach the region in which the subject to be detected is immobilized.

Preferably, the electrode may be provided on the support, and the subject to be detected may be immobilized in a region having a diameter of several tens to several hundreds of μm.

Preferably, the subject to be detected may be immobilized in a region having a diameter of several tens to several hundreds of μm, and the electrode may surround the region.

Preferably, the support may be a material selected from the group consisting of glass, ceramics, noble metals, and resins.

In one embodiment, the device of the present invention may further comprise means for promoting the fixing of the subject to be detected.

In one embodiment, the promoting means may be used to stir the solution in the cell.

In one embodiment, the promoting means may be used to exchange the solution in the cell.

In one embodiment, the promoting means may be used to supply the solution in the cell.

In one embodiment, the promoting means may be used to allow the solution to flow through the cell.

BRIEF DESCRIPTION OF THE DRAWINGS

FIG. 3 schematically shows the principle of the present invention.

FIG. 8 shows an exemplary support used in the present invention.

FIG. 9 shows an exemplary support used in the present invention.

FIG. 13(a) shows a plan view and a cross-sectional view of a device in which the region, in which the subject to be detected is immobilized, is provided on a portion of an electrode disposed on the base plate.

FIG. 13(b) shows a plan view and a cross-sectional view of a device in which the region, in which the subject to be detected is immobilized, is provided at the middle of a doughnut-shaped electrode disposed on the base plate.

FIG. 13(c) shows a plan view and a cross-sectional view of a device in which the region, in which the subject to be detected is immobilized, is provided on the base plate and at the middle of a doughnut-shaped electrode disposed on the base plate.

FIG. 14 schematically shows an embodiment of the present invention.

FIG. 15(a) is a conceptual diagram showing a means for stirring a solution for promoting the fixing of the subject to be detected to a support (Embodiment 9).

FIG. 15(b) is a conceptual diagram showing a means for vibrating a solution for promoting the fixing of the subject to be detected to a support (Embodiment 9).

FIG. 15(c) is a conceptual diagram showing a means for vibrating a support for promoting the fixing of the subject to be detected to the support (Embodiment 9).

FIG. 16 schematically shows an embodiment of the present invention.

FIG. 17 schematically shows the principle of measurement performed by the sensor device of the present invention.

BEST MODE FOR CARRYING OUT THE INVENTION

The present invention relates to a sensor device comprising at least one support for immobilizing a subject to be detected, and a cell for containing a solution in which a reaction product generated from the subject to be detected is diffused, wherein at least one reaction region having a constant concentration of the reaction product is formed by diffusion of the reaction product into the solution, and the reaction region is formed in such a manner that the reaction product is specifically detected in a predetermined measurement time.

Figure 1:
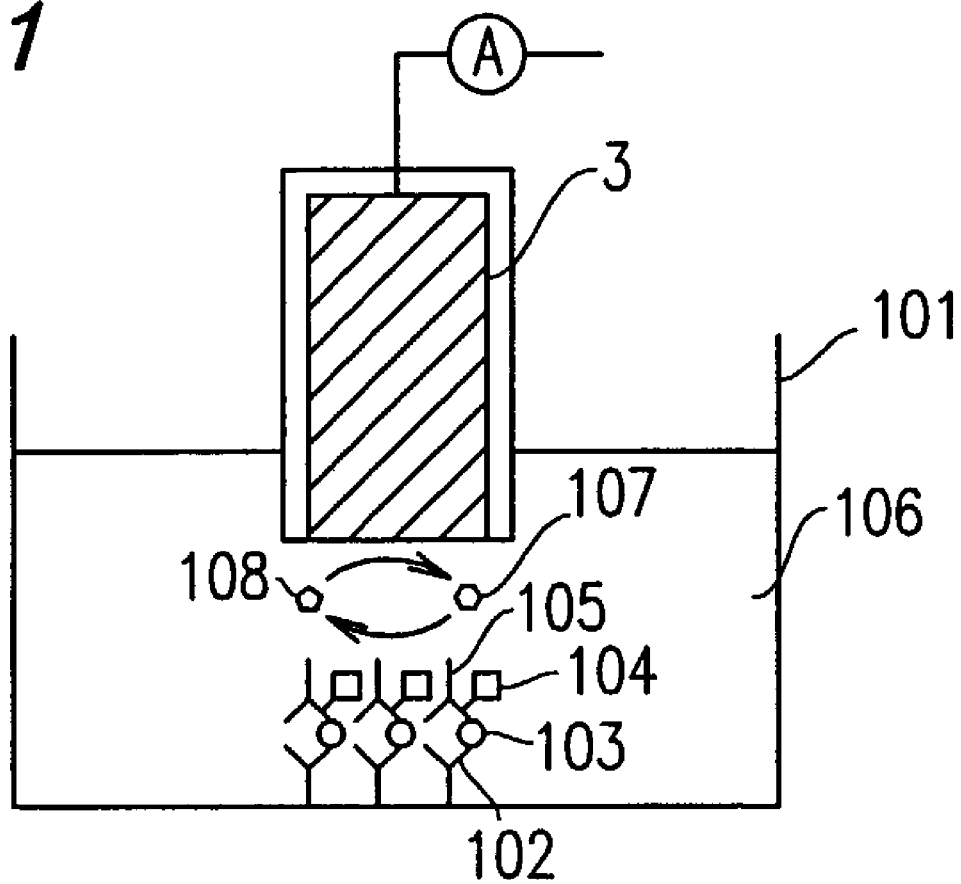
FIG. 1 schematically shows a sensor device according to the present invention.
Figure 2:
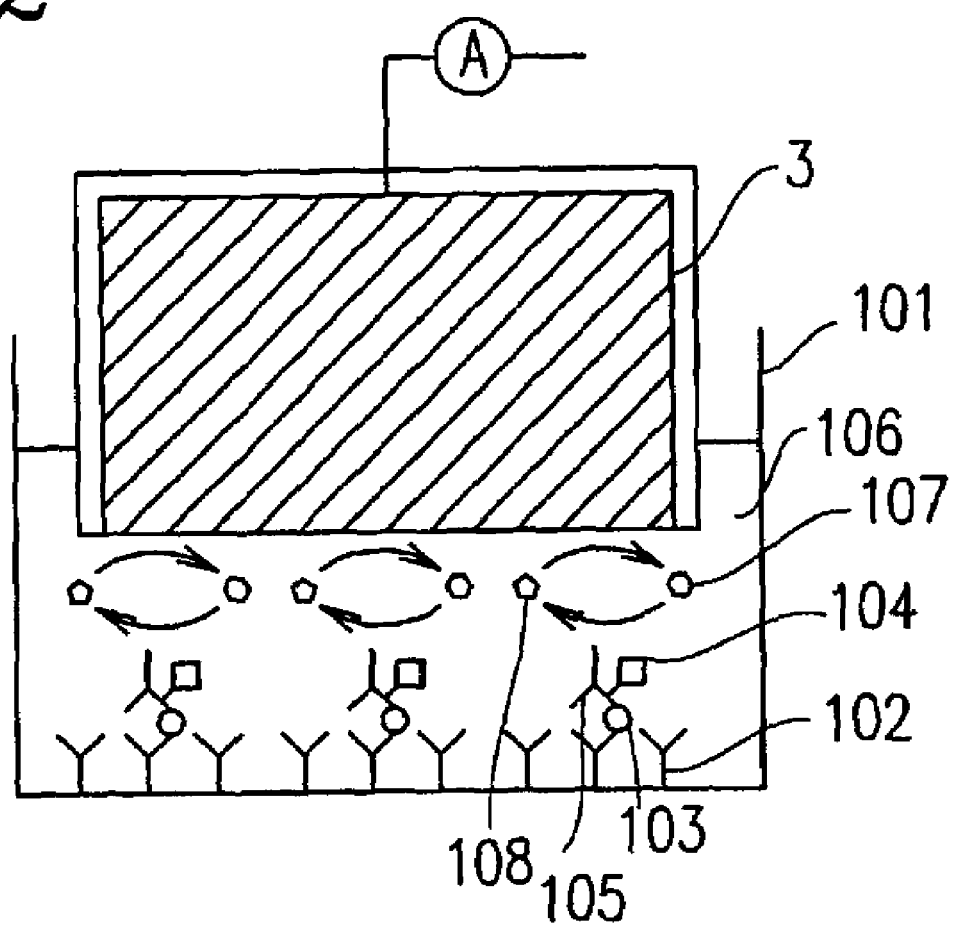
FIG. 2 schematically shows a conventional immunosensor device.

FIG. 1 shows an example according to Embodiment 1 of the present invention. Note that in explaining FIG. 1 below, for the sake of simplicity, reference numerals in the figure, which correspond to the same portions as those in a conventional example (FIG. 2), are indicated by the same numerals.

As shown in FIG. 1, antibodies 102 are immobilized on a portion of a bottom surface of a detection cell 101. In this embodiment, the size of the region in which the antibodies are immobilized is limited to a diameter of several tens of μm to several hundreds of μm. For this reason, an electrode can be used to detect an enzyme reaction product rapidly and specifically.

In general, a key factor for achieving rapid and specific detection is to efficiently conduct a reaction of a labeled enzyme, which is immobilized by a complex formation reaction among an analyte, an immobilized antibody and an enzyme labeled antibody, with an enzyme substrate contained in a solution.

In this embodiment, the size of the region in which the antibodies are immobilized is limited to a small range having a diameter of several tens of μm to several hundreds of μm. Thereby, reaction of the labeled enzyme with the substrate, and oxidation and reduction reactions of the enzyme reaction product by the electrode, do not depend on the diffusion rate of each substance in the solution, and reactions, which sequentially cycle from the reaction of the enzyme with the substrate to the oxidation and reduction reactions of the enzyme reaction product, are conducted within the very small region. As a result, the enzyme reaction product is detected rapidly and specifically.

Moreover, the region, in which detection is performed by the electrode, has substantially the same size as that of the region in which the antibodies are immobilized. Thereby, a noise component generated outside the antibody-immobilized region is not substantially detected. As a result, only enzyme reactions occurring in the vicinity of the antibody-immobilized region are efficiently detected, thereby making it possible to perform measurement at a high S/N (signal to noise) ratio.

In practical situations, in order to prepare the antibody-immobilized region with precision and to position the electrode with respect to the region with precision, an appropriate size of the antibody-immobilized region is a diameter of several tens of μm to several hundreds of μm. When the antibody-immobilized region is smaller than that size, it is difficult to accurately position the electrode with respect to the region. When the antibody-immobilized region is larger than that size, it takes from several tens of minutes to several hours for a reaction region of the enzyme reaction product to be formed, as described below with reference to FIG. 3. Therefore, as shown in this embodiment, in order to achieve rapid and specific measurement while keeping the advantages of the enzyme electrode immunosensor device, i.e., "simple structure and rapid detection", the size of the antibody-immobilized region is limited to a diameter of several tens of μm to several hundreds of μm.

In the above-described example, the antibodies are immobilized on the support. Either antigens or antibodies are immobilized on the support, depending on the purpose. A subject to be detected is a labeled antibody bound to an analyte, or an enzyme which is linked via an antibody to an analyte.

FIG. 3 is a schematic diagram showing the principle of the present invention. The present invention is not constrained by any principle. For the sake of simplicity of understanding of the present invention, the present invention will be described with reference to FIG. 3. The column to the left of FIG. 3 shows a time course of how a reaction product (e.g., an enzyme reaction product), which is generated in a region 2 on a base plate 1 in which a subject to be detected is immobilized, is diffused in a solution to form a reaction region 5 (after 1 second, 100 seconds, and 1,000 seconds of reaction).

The reaction region 5 becomes a layer having a thickness of about 10 μm after 1 second of the reaction, a layer having a thickness of about 100 μm after 10 seconds of the reaction, and a layer having a thickness of about 1000 μm after 1,000 seconds of the reaction, for example. The reaction within the reaction region is continued as long as a reaction substrate is supplied from the solution. The production of the reaction product within the reaction region and the diffusion of the reaction product from the reaction region to the solution reach equilibrium after a predetermined time (typically called a measurement time). As a result, a region 5' having a substantially constant size and a constant concentration of the reaction product is formed. As used herein, the term "reaction region" representatively refers to a region 5' having a generally constant concentration of a reaction product at a predetermined time after the start of a reaction beginning with the addition of the reaction substrate (i.e., the start of the diffusion of the reaction product).

Figure 4A:
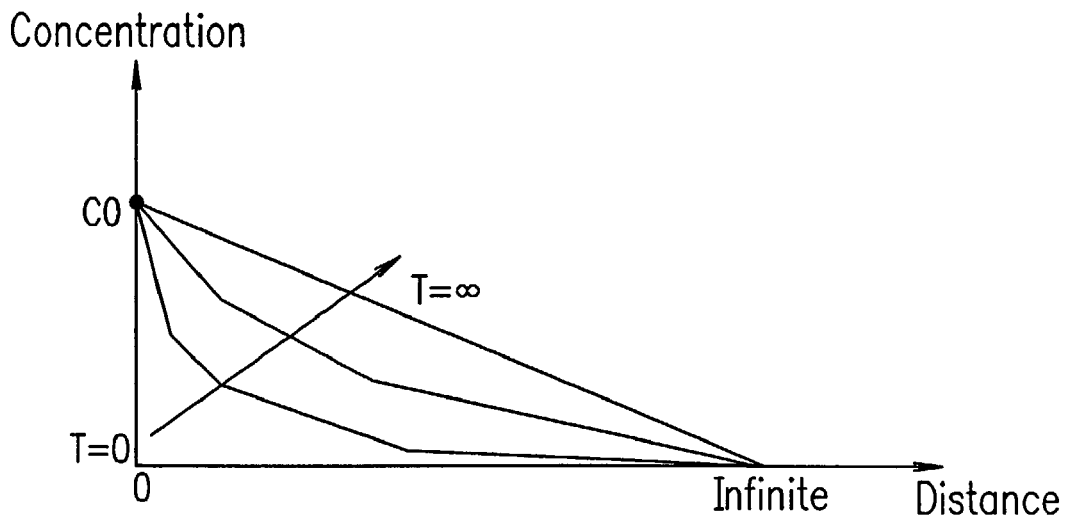
FIG. 4A schematically shows the principle of the present invention.
Figure 4B:
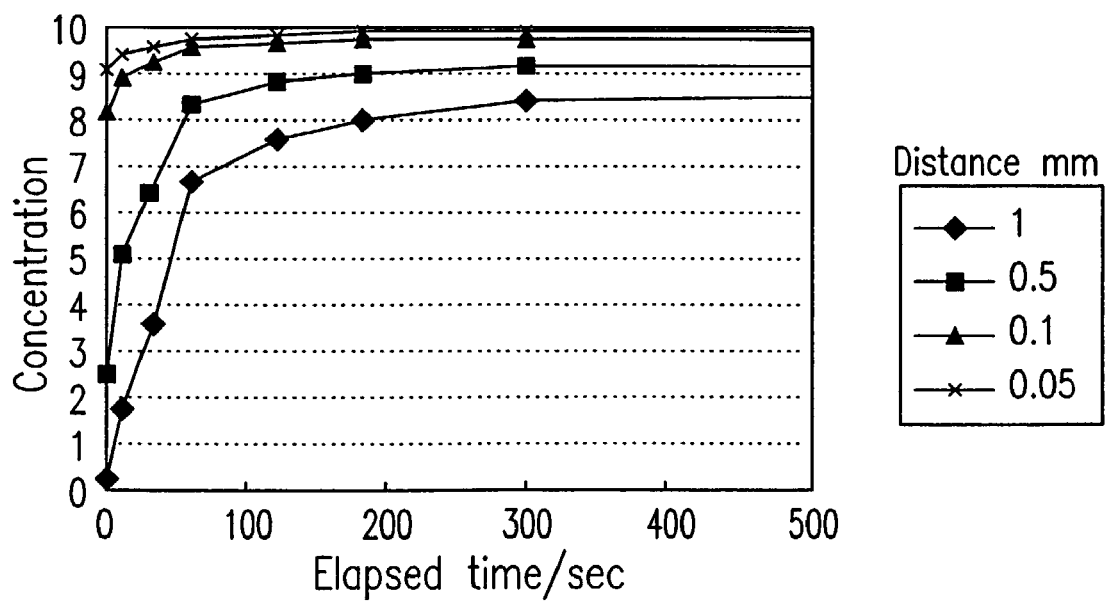
FIG. 4B is a graph showing the principle of the present invention.
Figure 4C:
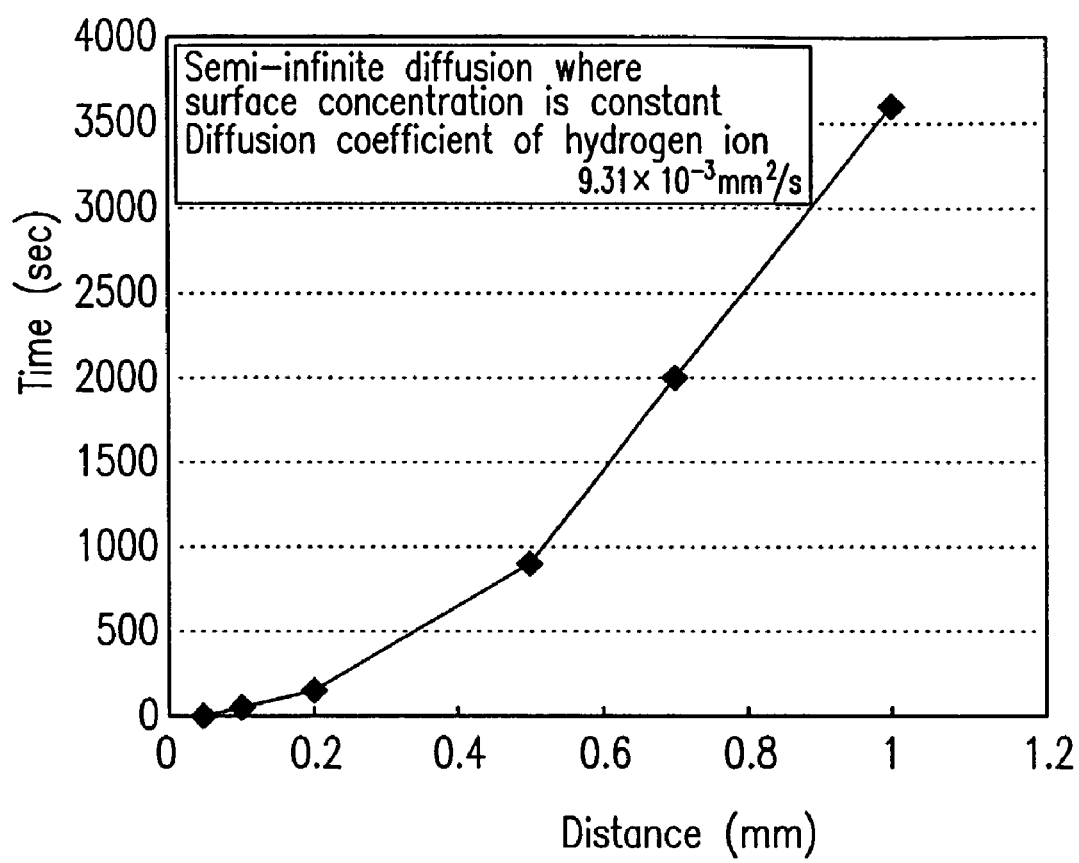
FIG. 4C is a graph showing the principle of the present invention.

FIG. 4C is a diagram representing the size of the reaction region theoretically as a distance from the reaction site which is a function of time. FIG. 4C shows the size of the reaction region when hydrogen ion is diffused semi-infinitely in the solution, for example. The reaction region can be considered to be a region enclosed with a surface having a constant concentration of hydrogen ion at a predetermined time after the start of the diffusion.

In general, hydrogen ion concentration at distance X from the reaction site (the starting point of the diffusion) after time T is represented by the equation: $C=C_0 \times erf(X/2 \times DT^{0.5})$; where $C_0$ represents an initial concentration of hydrogen ion at the diffusion starting point; C represents a hydrogen ion concentration (surface concentration) at distance X and time T; D represents the diffusion coefficient of a hydrogen ion ($9.31 \times 10^{-3}$ mm$^2$/sec); and erf represents an error function. The plot of the equation substantially forms FIG. 4A.

Assuming that the surface concentration of hydrogen ion is 10 (the hydrogen ion concentration within the reaction region is considered to be constant and in an equilibrium state), changes over time of the hydrogen ion concentration at predetermined distances (1 mm, 0.5 mm, 0.1 mm, and 0.05 mm) are plotted in FIG. 4B according to the above-described equation. In FIG. 4B, a diamond represents a plot of the hydrogen ion concentration at a distance of 1 mm, a square represents a plot at a distance of 0.5 mm, a triangle represents a plot at a distance of 0.1 mm, and x represents a plot at a distance of 0.05 mm. Next, the time at which the hydrogen ion concentration reaches 9 (i.e., the hydrogen ion concentration is substantially in an equilibrium state) is plotted with respect to a distance in the graph of FIG. 4C. As can be understood from this graph, when the measurement time is 30 minutes, the reaction region is 0.6 to 0.7 mm thick with reference to the reaction site, i.e., the diffusion starting point; when the measurement time is 10 minutes, the reaction region is 0.3 to 0.4 mm thick; when the measurement time is 5 minutes, the reaction region is 0.2 to 0.3 mm thick; when the measurement time is 3 minutes, the reaction region is 0.1 to 0.2 mm thick; and when the measurement time is 1 minute, the reaction region is about 0.1 mm thick.

Referring again to FIG. 3, the column to the right of FIG. 3 shows a time course of how a detection means 3 (e.g., an electrode) reaches a stable operational state, corresponding to the column to the left of FIG. 3. When the detection means 3 is actuated, the thickness of a detection region 7, in which a subject to be detected is detected, becomes larger overtime. It takes a predetermined time until the detection means 3 operates stably. In the example shown in the column to the right of FIG. 3, the thickness of the reaction region 7 reaches a constant state about 100 seconds after the start of the actuation (indicated by 7' in the column to the right of FIG. 3).

As used herein, the term "detection region" of a detection means refers to the detection region 7' having a generally constant size.

In the present invention, the size of the region 2 in which the antibodies are immobilized is set to a diameter of several tens of μm to several hundreds of μm, so that the detection region 7' and the reaction region 5' are arranged in a relative positional relationship such that a reaction product can be detected rapidly and specifically. Therefore, the detection region 7' may be disposed in such a manner as to include or overlap the reaction region 5'. Alternatively, the detection region 7' is disposed in such a manner as to be included in the reaction region 5'.

Antibodies used in the present invention may be immobilized on the support by a method well known to those skilled in the art. The antibodies may be immobilized in a predetermined region in high density without impairing their functions. The density of immobilized antibodies may be increased by roughening the smoothness of the surface of the support by physical or chemical means. By treating the support with an appropriate surface treatment reagent, the density of immobilized antibodies may be increased.

In the example of Embodiment 1 shown in FIG. 1, the reaction region faces the electrode. The reaction region and the electrode may be provided on the same support, for example.

In the example of Embodiment 1 shown in FIG. 1, an immunosensor is provided, in which an antigen-antibody reaction is detected by an enzyme reaction. The present invention is not so limited. For example, the sensor device of the present invention may be a sensor device for detecting the activity of microorganisms, in which the cells of the microorganisms are immobilized on a support and their activities are detected based on changes in oxygen concentration around the microorganism. Further, the sensor device of the present invention may be a protein sensor device in which an analyte is specifically captured or detected with a reaction other than an antigen-antibody reaction. Moreover, the sensor device of the present invention may be a toxin sensor for detecting a toxin or the like in a specimen, in which a support is made of a synthetic lipid membrane or the like.

Figure 5:
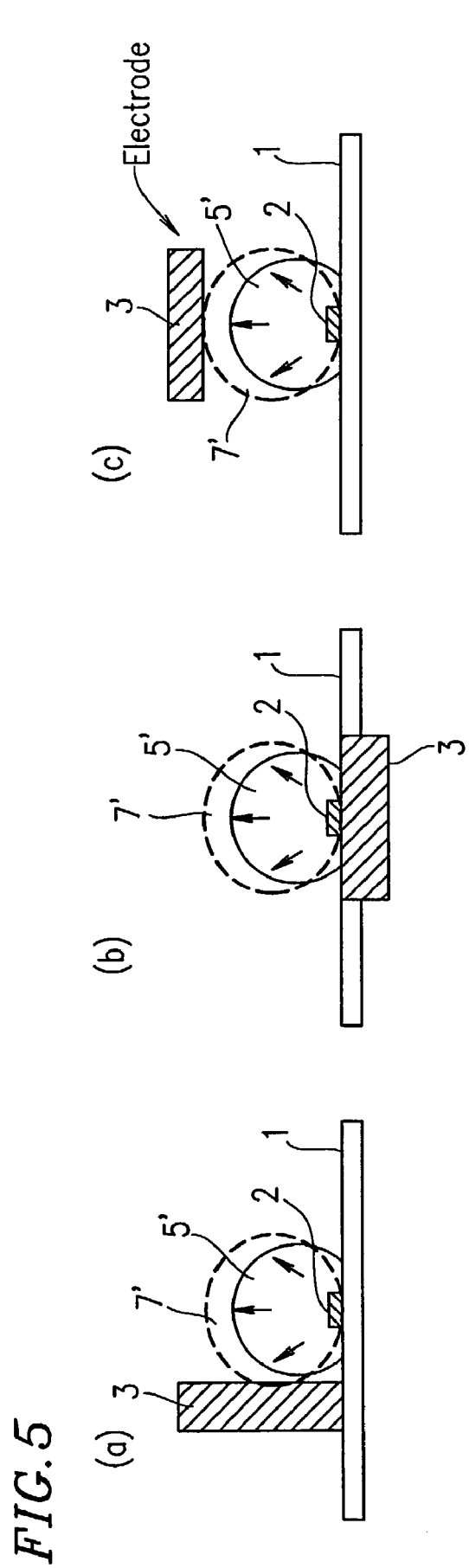
FIG. 5(a) schematically shows an embodiment of the present invention in which the detection means is disposed on the support and adjacent the reaction region (Embodiment 3).
FIG. 5(b) schematically shows an embodiment of the present invention in which the detection means is disposed on or within the support (Embodiment 2).
FIG. 5(c) schematically shows an embodiment of the present invention in which the detection means is disposed so as to face the immobilized region on the support (Embodiment 1).

FIG. 5 schematically shows embodiments of the present invention. As shown in FIGS. 5(a), (b) and (c), in the present invention, as long as the reaction region 5' and the detection region 7' are disposed in such a manner that a reaction product can be detected rapidly and specifically, the detection means 3 may be disposed in such a manner as to face the immobilized region 2 on the support 1 (FIG. 5(c): Embodiment 1), the detection means 3 may be disposed on or within the support 1 (FIG. 5(b); Embodiment 2), or the detection means 3 may be disposed on the support and adjacent to the reaction region 2 (FIG. 5(a); Embodiment 3).

Figure 6:
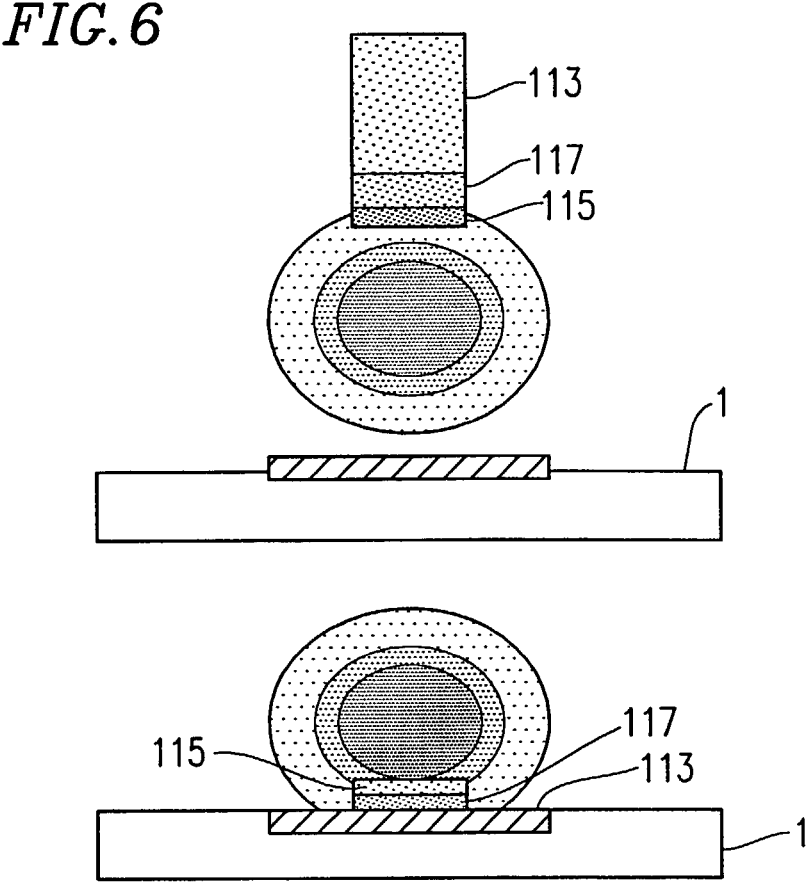
FIG. 6A schematically shows an embodiment of the present invention in which the subject to be detected is immobilized via a fixing means on the detection means, and the detection means is disposed so as to face the support plate (Embodiment 1).
FIG. 6B schematically shows an embodiment of the present invention in which the subject to be detected is immobilized via a fixing means on the detection means, and the detection means is disposed within the base plate (Embodiment 2).

FIG. 6B is a schematic diagram showing Embodiment 2 of the present invention in comparison with Embodiment 1 of the present invention, which is shown in FIG. 6A. In Embodiment 2, a detection means 113 is disposed within a base plate, and a subject to be detected 115 is immobilized on the detection means 113 via a fixing means 117. Concentric ellipses shown in FIGS. 6A and 6B represent detection regions of the detection means 113.

Figure 7:
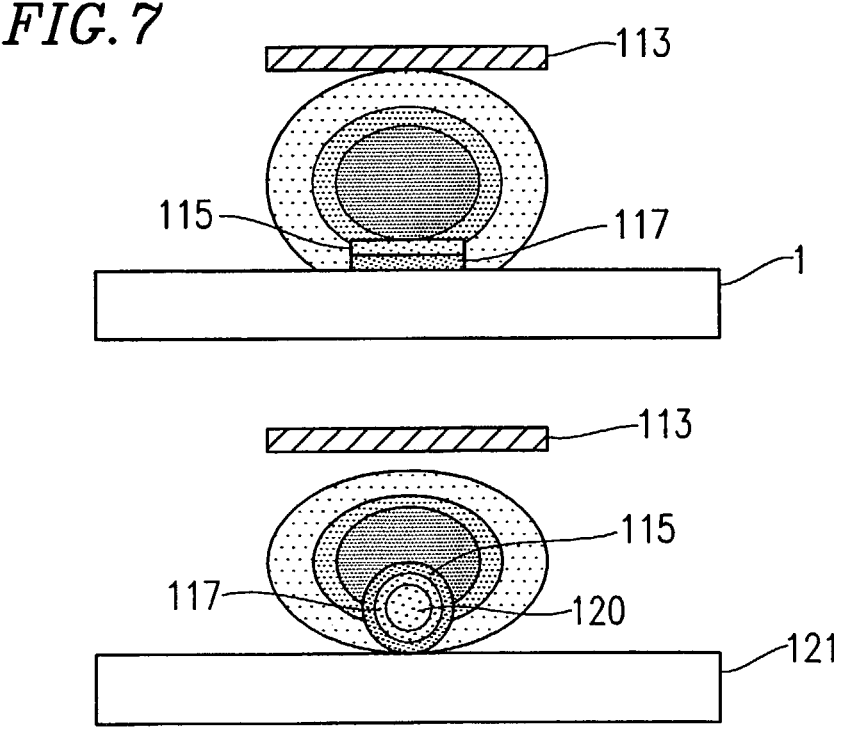
FIG. 7A schematically shows an embodiment of the present invention in which the subject to be detected is immobilized via a fixing means on the support means, and the detection means is disposed so as to face the support means (Embodiment 1).
FIG. 7B schematically shows an embodiment of the present invention in which the subject to be detected is immobilized via a fixing means on the support means in the shape of a particulate other than a base plate, and the detection means is disposed so as to face the support means (Embodiment 4).

FIG. 7B is a schematic diagram showing Embodiment 4 of the present invention (as sensor device employing a support other than a base plate; a device shown in FIG. 7A) in comparison with Example 1 of the present invention. In Embodiment 4, the subject to be detected 115 is immobilized via a fixing means 117 on a support 120 in the shape of, for example, a particulate other than a base plate. Ellipses shown in the figure represent detection regions of the detection means 113. In the FIG. 7B, the particulate support 120 is shown as a single particulate disposed on a bottom surface 121 of a cell, or alternatively, there may be a plurality of particulate supports. For example, Embodiment 4 of the present invention may comprise a tubular cell containing a plurality of particulate supports therein. Alternatively, as shown in FIGS. 8A and 8B, a cluster of particulate supports may be disposed on the cell (shown in FIG. 8A), or means 116 for collecting particulate supports into a specific region in the device may be provided (shown in FIG. 8B).

The support used in Embodiment 4 of the present invention may be optionally in any shape. FIG. 9A schematically shows a particulate support 120 and FIG. 9B shows a rod shaped support 112 with a subject to be detected 115 fixed via a fixing means 117.

The device of the present invention may optionally comprise any detection means known to those skilled in the art.

Figure 10:
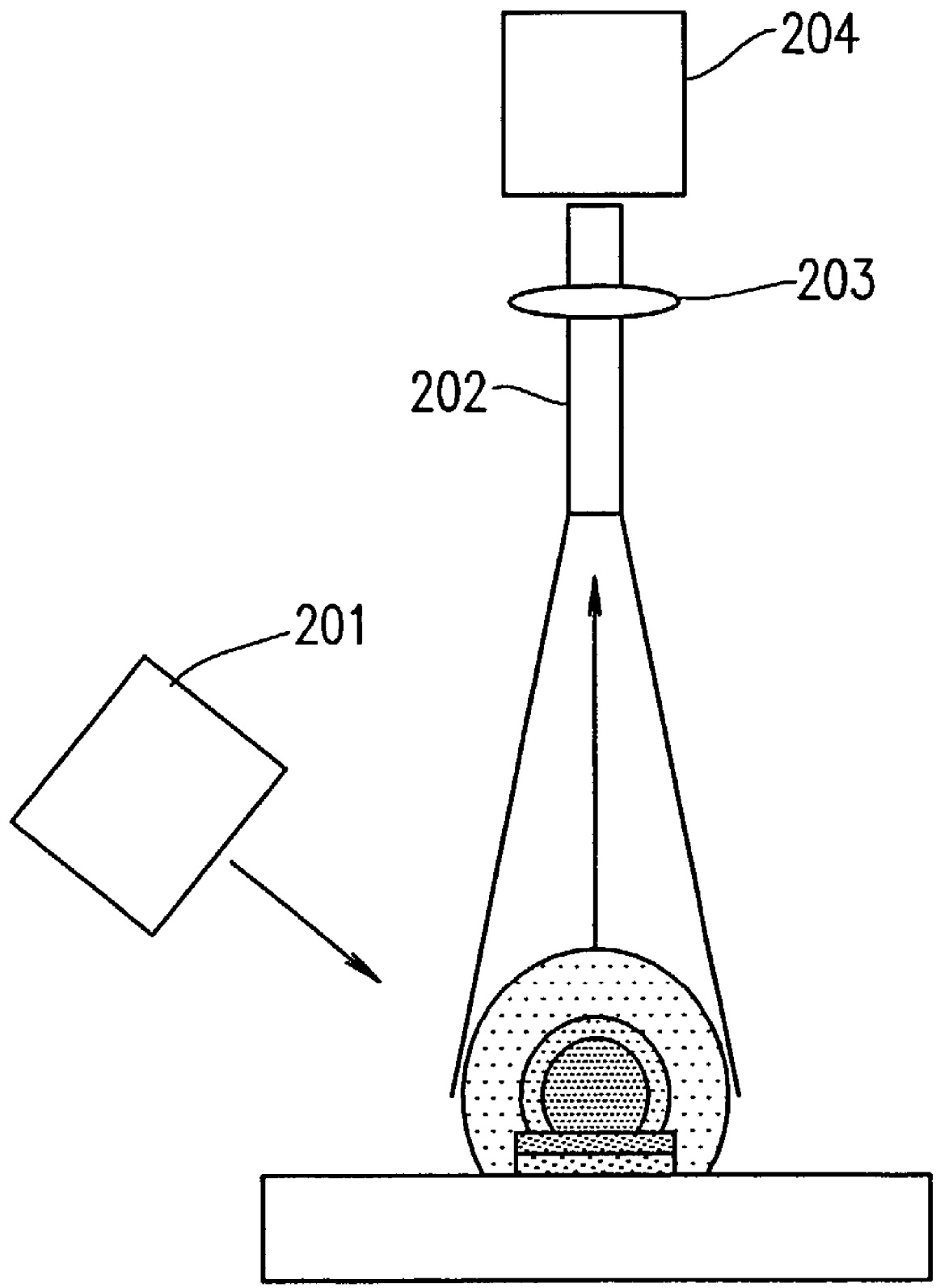
FIG. 10 schematically shows an embodiment of the present invention.

FIG. 10 schematically shows Embodiment 5 of the present invention employing a CCD as a detection means. In this embodiment, a reaction product in a reaction region is detected by irradiating the reaction product with ultraviolet light from a light source 201, collecting light emitted from the reaction product using a glass fiber 202, and detecting the light using a CCD 204.

Figure 11:
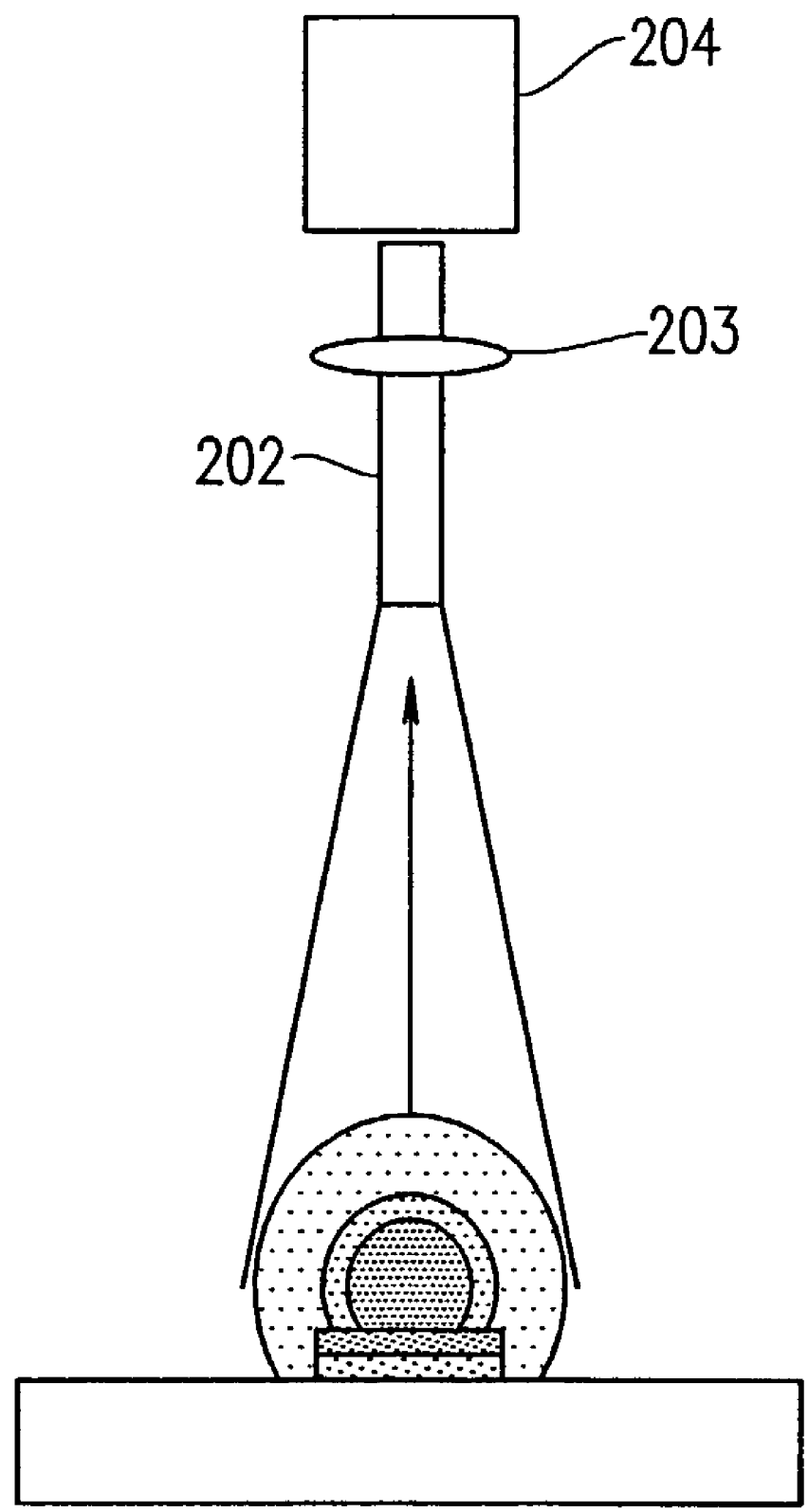
FIG. 11 schematically shows an embodiment of the present invention.

FIG. 11 schematically shows Embodiment 6 of the present invention. In this embodiment, a reaction product in a reaction region is detected by collecting light emitted by the reaction product itself using a glass fiber 202 and a lens 203, and detecting the light using a CCD 204.

Figure 12:
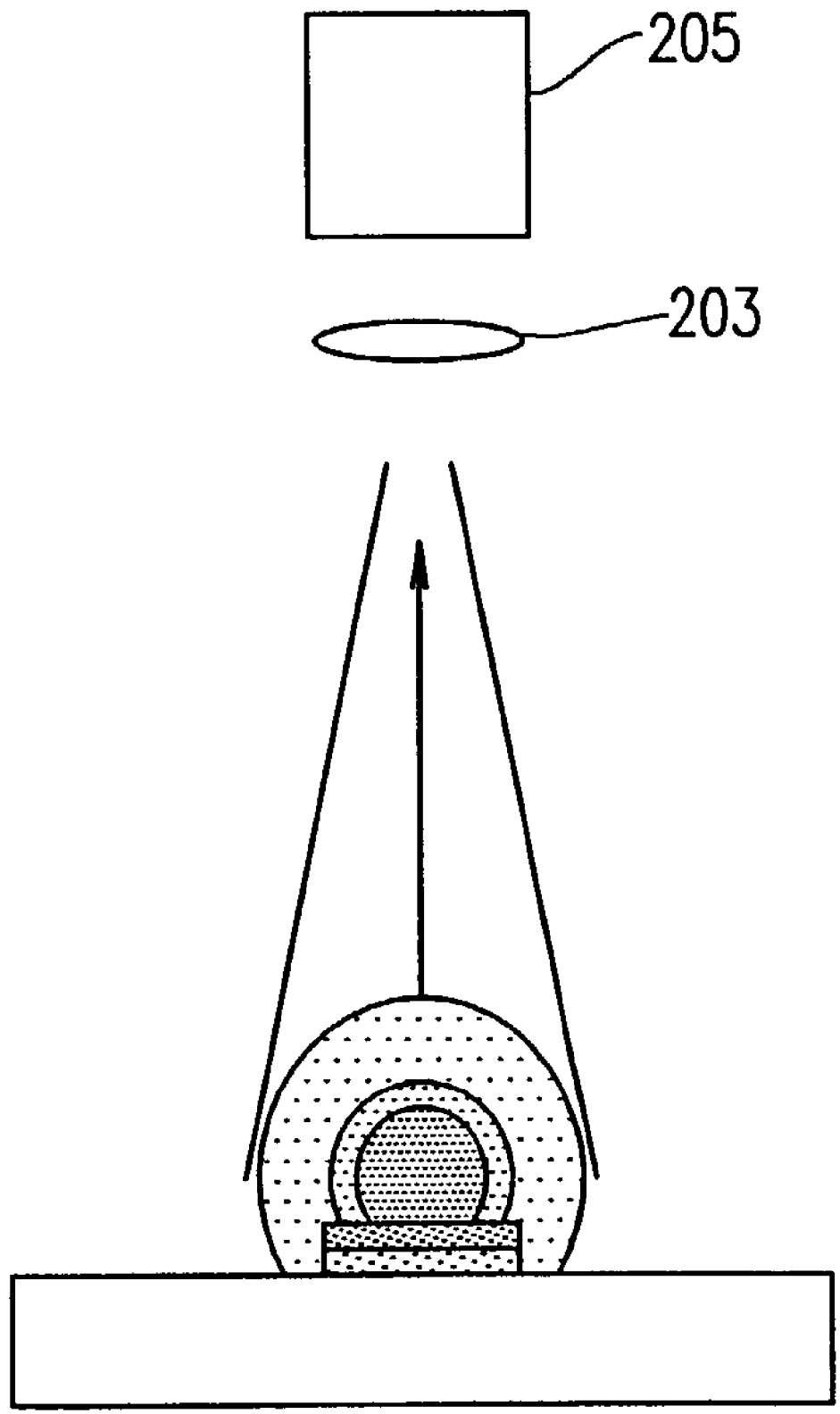
FIG. 12 schematically shows an embodiment of the present invention.

FIG. 12 schematically shows Embodiment 7 of the present invention. In this embodiment, a reaction product in a reaction region is detected by collecting heat (infrared light) emitted by the reaction product itself, and detecting the heat using a pyroelectric sensor 205.

FIG. 13 shows a variant of Embodiment 2 of the present invention. FIG. 13(a) shows a plan view and a cross-sectional view of a device in which a region 2, in which a subject to be detected is immobilized, is provided on a portion of an electrode 3 disposed on a base plate 1. FIG. 13(b) is a plan view and a cross-sectional view of a device in which a region 2, in which a subject to be detected is immobilized, is provided at the middle of a doughnut-shaped electrode 3 disposed on a base plate 1, and on a support structure 207 of the electrode 3. FIG. 13(c) is a plan view and a cross-sectional view of a device in which a region 2, in which a subject to be detected is immobilized, is provided at the middle of a doughnut-shaped electrode 3 disposed on a base plate 1, and on the base plate 1.

Note that materials for the members of the devices according to the above-described embodiments of the present invention may be any material used in conventional sensor devices, which are known to those skilled in the art, unless otherwise specified. Members known in the art can be used as the devices and members used in the above-described embodiments of the present invention, such as a CCD, a glass fiber, an ultraviolet light source, and a pyroelectric sensor.

FIG. 14 is a conceptual diagram showing Embodiment 8 of the present invention. In this embodiment, a detection means 209 is allowed to approach a support 1 in a direction indicated by an arrow when detecting a reaction product. Any arrangement known in the art may be used so as to allow the detection means 209 to approach the base plate 1.

FIG. 15 is a conceptual diagram showing Embodiment 9 of the present invention. In this embodiment, a means 215 (not shown) is provided for promoting the fixing of a subject to be detected 115 to a support 1. As the means 215, a means for stirring or vibrating a solution, such as a stirring rod (FIG. 15(*a*) or (*b*)), or a means for vibrating a support (FIG. 15(*c*)) may be used. Any arrangement known in the art may be used as the means 215 for promoting the fixing of the subject to be detected 115 to the support 1.

FIG. 16 is a conceptual diagram showing a variant of Embodiment 9 of the present invention. In this variant, as the means 215 (not shown) for promoting the fixing of the subject to be detected 115 to the support 1, a means for loading and unloading a solution in a cell, a means for exchanging a solution in a cell, a means for keeping on supplying a solution to a cell, and a means for flowing a solution through a cell, may be used. These means are known in the art.

EXAMPLES

The present invention will be described by way of examples. The examples below are only illustrations of the present invention. The present invention is not so limited.

Example 1

Optimization of Detection Means

Figure 21A:
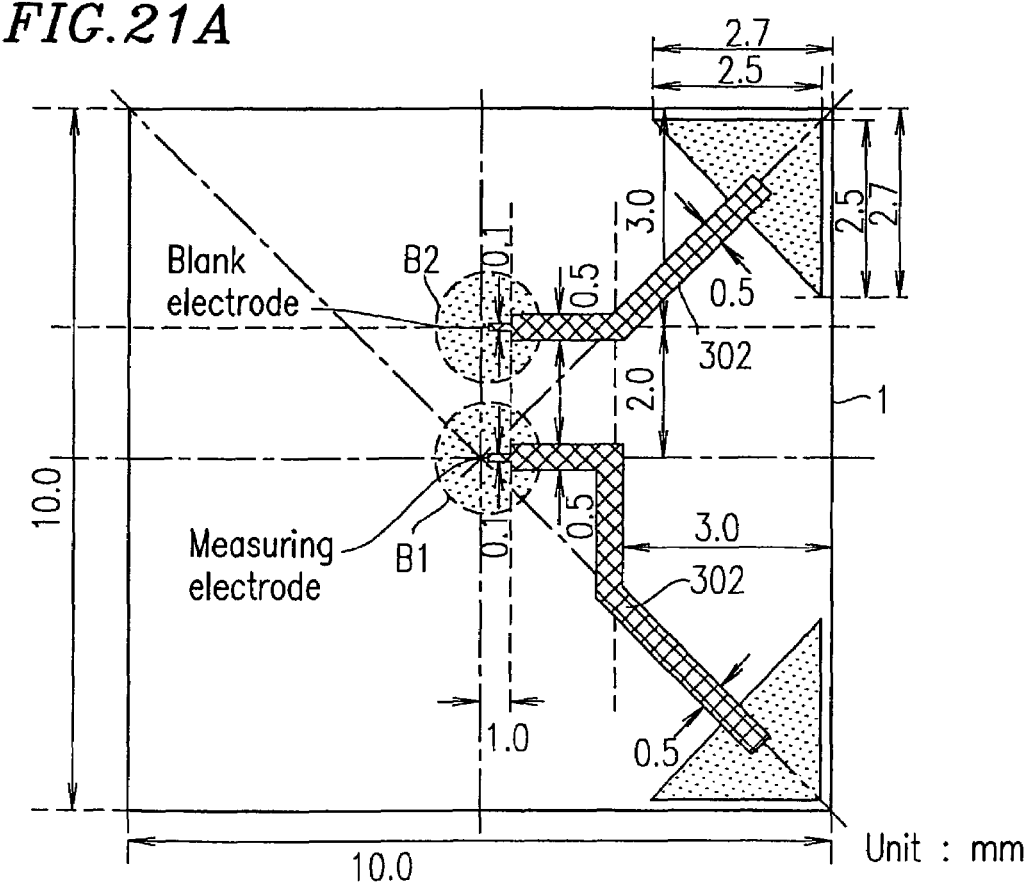
FIG. 21A is a plan view showing a sensor device according to the present invention.
Figure 21B:
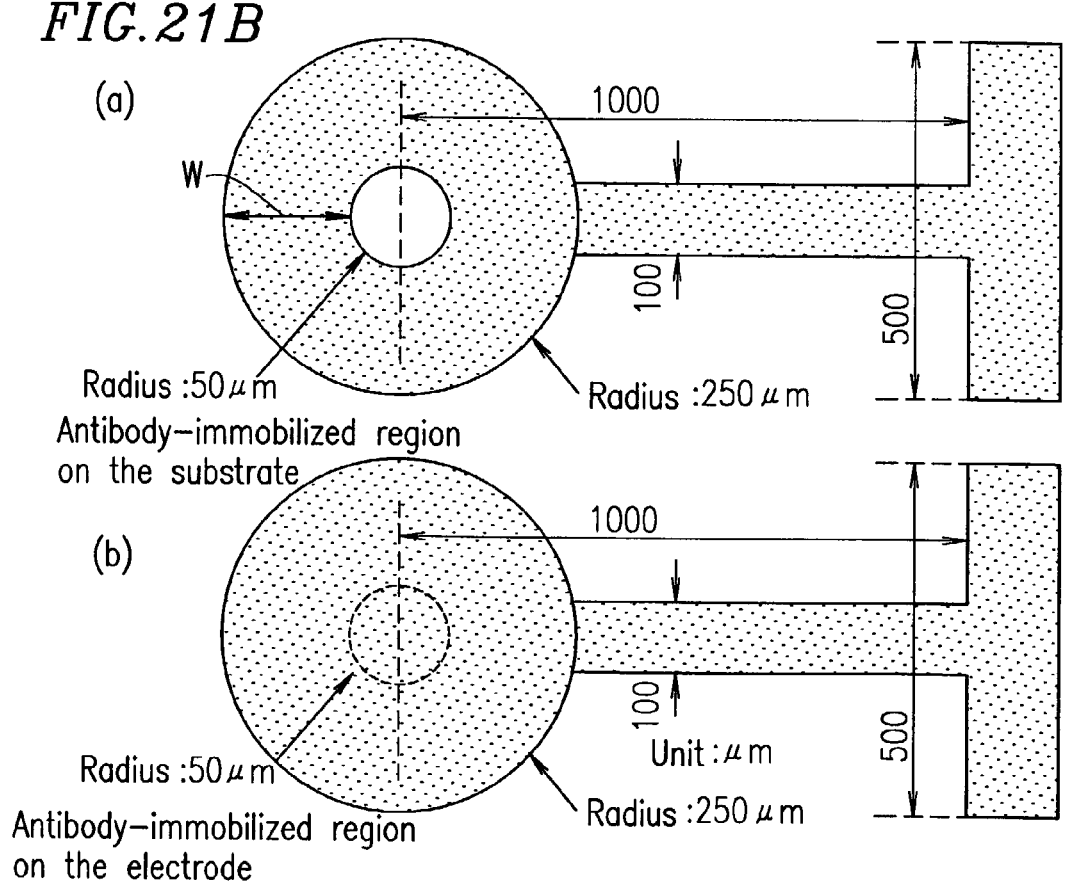
FIG. 21B is an enlarged view showing an electrode portion of the sensor device of the present invention.

Firstly, as the above-described electrodes 3, a set of electrodes having a shape shown in FIG. 21B(*a*) were prepared, where they are different from each other only in the electrode width (W) (by depositing gold on a base plate). Each of the prepared electrodes was set in a sensor device having a structure as schematically shown in FIG. 17 (note that secondary antibodies for ELISA were immobilized). The current response time of each electrode was measured under the following conditions.

(Measurement Conditions)

Immobilized antibody: secondary antibody for ELISA (labeled with horseradish peroxidase (HRP)).

Immobilized region: diameter 100 µm, 0.5 mg/ml of a solution containing secondary antibodies for ELISA was dropped and immobilized.

Composition of reaction solution: ferrocene methanol (FMA), 0.5 mM; $H_2O_2$, 5 mM; KCl, 0.1 M; disodium hydrogen phosphate, 0.1 M.

Figure 18:
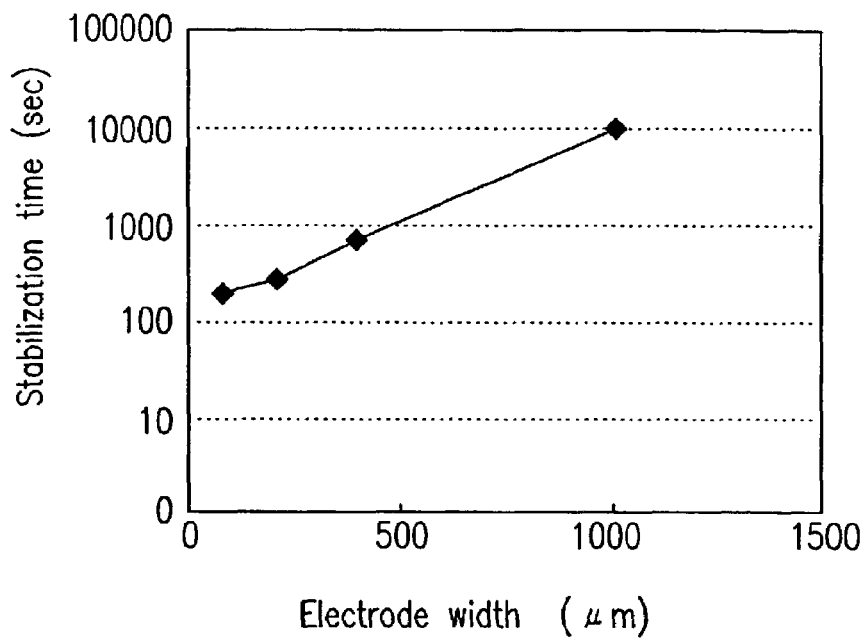
FIG. 18 shows a graph indicating the relationship between the width of an electrode and the time required to stabilize the electrode.

As shown in FIG. 17, in this evaluation system, a current generated by an oxidation-reduction reaction of FMA coupled with an enzyme reaction was detected to evaluate the performance of each electrode. The test results are shown in FIG. 18. In FIG. 18, the horizontal axis represents electrode width (µm), which is the width W of the doughnut of the doughnut-shaped electrode shown in FIG. 21B(a). In FIG. 18, the vertical axis represents the stabilization time of the electrode. Note that the stabilization time of the electrode is defined as a time in which 90% of the maximum current value is obtained. As indicated in FIG. 18, when the electrode had a width of 100 µm, the stabilization time was about 300 seconds. The greater the electrode width, the greater the time required for stabilization. The electrode having a radius of 1,000 µm (1 mm) required about 10,000 seconds (about 2.8 hours).

Practically speaking, it is considered that an appropriate measurement time is typically within about 1,000 seconds. Therefore, the electrode width needs to be less than about 500 µm.

Figure 19:
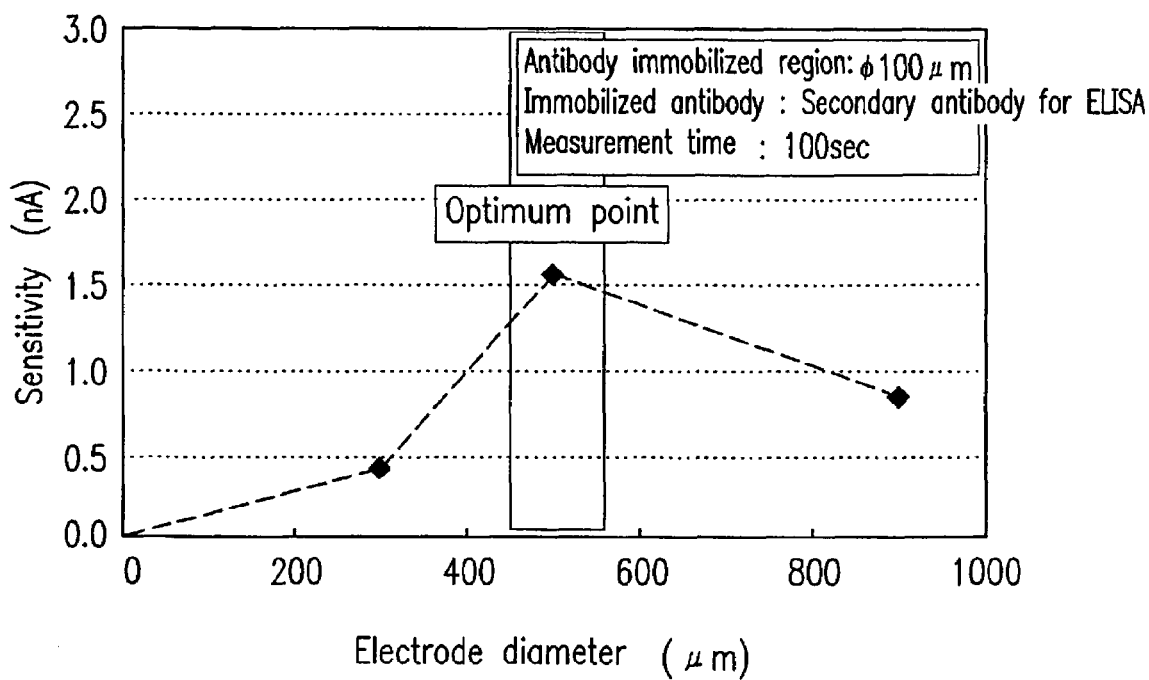
FIG. 19 shows a graph indicating the relationship between the diameter of an electrode and the sensitivity of the electrode.

Next, the same set of electrodes as above were used to conduct measurement under the same conditions as above, except that the measurement time was fixed to about 100 seconds, thereby determining the sensitivity of the electrodes. The results are shown in FIG. 19. In FIG. 19, the horizontal axis indicates the electrode diameter (µm) and the vertical axis indicates the electrode sensitivity. The electrode sensitivity is represented by the difference between an output current value when the secondary antibody for ELISA was immobilized and an output current value before the immobilization of the antibody.

As shown in FIG. 19, when the diameter of the electrode is smaller than or equal to about 500 µm, the electrode sensitivity increases with an increase in the electrode diameter. When the electrode diameter is about 500 µm, the electrode sensitivity reaches a maximum value. Over about 500 µm, the electrode sensitivity decreases.

Further, under the same conditions, the measurement time was elongated. The measurement results are summarized in FIG. 20.

Figure 20:
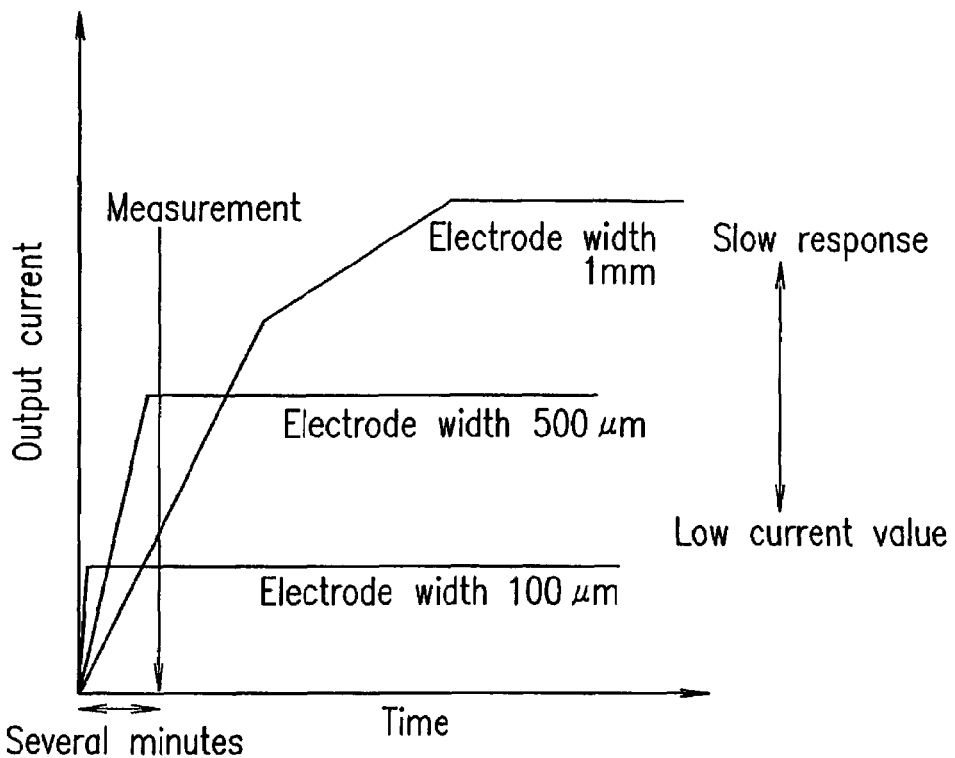
FIG. 20 shows a graph indicating the relationship between the times required for measurement and the output currents of electrodes having different widths.

In FIG. 20, the horizontal axis indicates the measurement time, and the vertical axis indicates an output current of the electrode. According to the results shown in FIG. 20, the greater the electrode width, the greater the output current. In this case, however, the response time is increased. The smaller the electrode width, the smaller the obtained output current. It is understood that if the measurement time and the electrode width are specified, an electrode width is uniquely determined.

According to the test results using the sensor device shown in this example, it is found that when the device had a reaction region having a diameter of about 100 µm, the optimum measurement sensitivity was obtained in the measurement taking about 1,000 seconds or less if an electrode having a width of about 500 µm was used.

Example 2

Preparation of Sensor Chip

FIG. 21A shows an exemplary sensor chip prepared according to the present invention. Dashed lines B1 and B2 surrounding substantially circular regions at the middle of FIG. 21A indicate regions in which the antibodies are immobilized. In the figure, two thick lines 302 indicate electrode lines, whose tips form a measuring electrode and a blank measuring electrode, respectively. Typically, these electrodes are formed by depositing gold or the like on the base plate 1. Note that numerical values in the figure represent dimensions of parts in units of mm.

FIG. 21B is a diagram showing detailed structures of the measuring electrode and the blank measuring electrode, which can be used in the device shown in FIG. 21A. FIG. 21B(a) shows a structure of a sensor chip in which a reaction region is provided on a base plate surrounded by an electrode, particularly indicating the vicinity of the electrode. FIG. 21B (b) shows an enlarged structure of a sensor chip in which a reaction region is provided on a surface of an electrode, particularly indicating the vicinity of the electrode.

In FIG. 21B(a), in a central circular region indicated as a white circle is a region having a radius of about 50 µm on the base plate, in which antibodies are immobilized. A doughnut-shaped electrode coated with gold is disposed in such a manner as to surround the region (a filled portion in the figure).

In FIG. 21B(b), an electrode whose circular region having a radius of about 250 µm entirely coated with gold is prepared. Antibodies are immobilized in a circular region having a radius of about 50 μm provided at the center of the electrode. Note that numerical values in the figure represent the dimensions of parts in units of μm.

Example 3

Preparation of Sensor Chip

Figure 22:
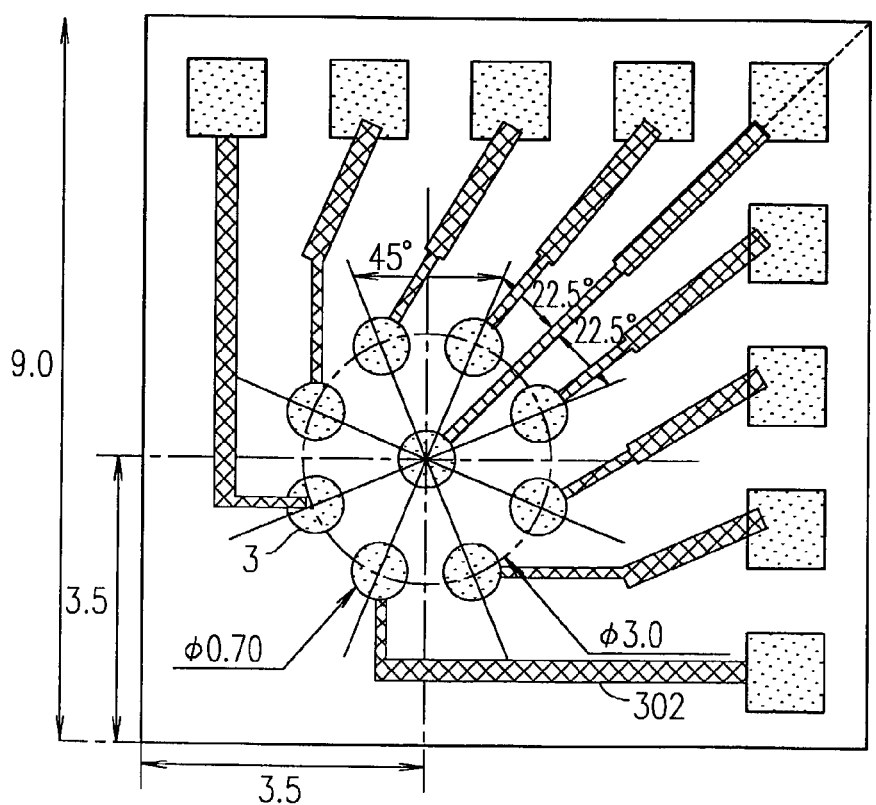
FIG. 22 is a plan view showing a sensor device according to the present invention.
Figure 23:
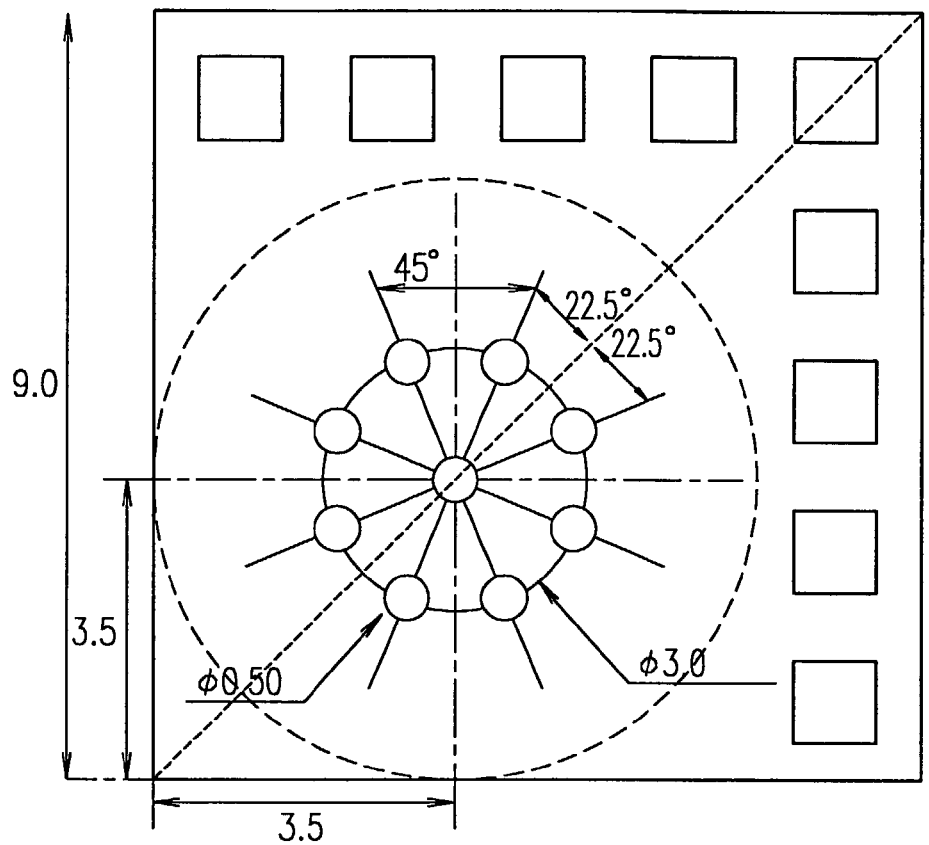
FIG. 23 is a diagram showing a resist pattern used in preparation of the sensor device of the present invention.
Figure 24:
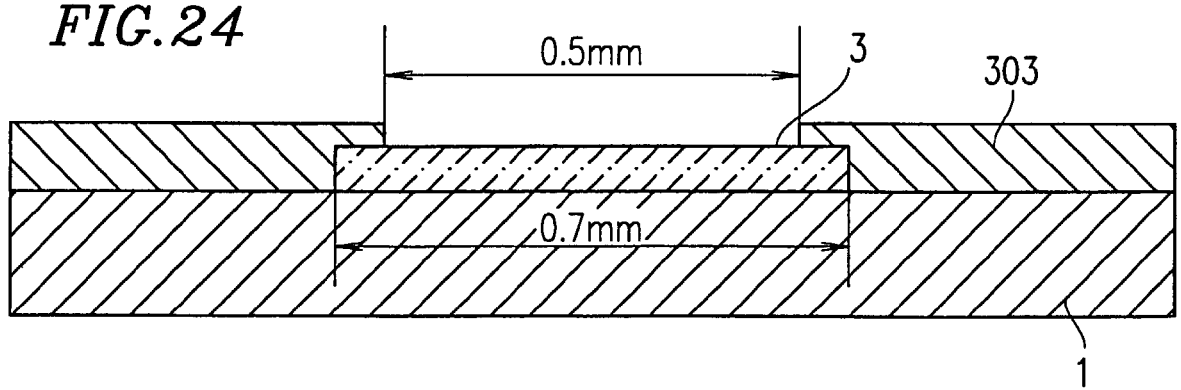
FIG. 24 is a cross-sectional view showing the sensor device of the present invention.
Figure 25:
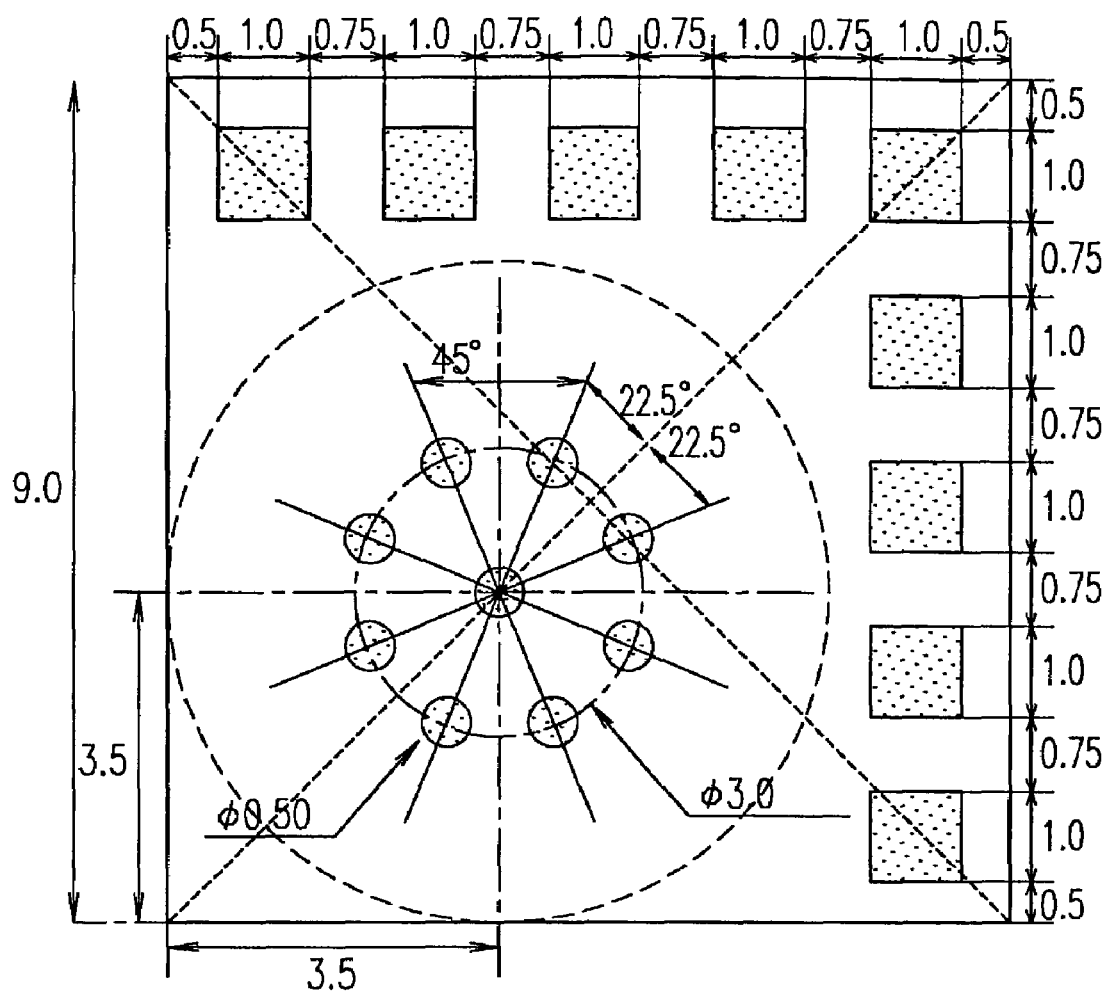
FIG. 25 is a plan view showing a sensor device according to the present invention.

FIG. 22 shows another structure of a sensor chip prepared according to the present invention. In the sensor chip, a plurality of electrodes were disposed on a base plate, and an antibody immobilized region was provided on each electrode. Nine circles provided in substantially the middle of the figure represent the electrodes. As can be seen, the 9 electrodes 3 were arranged in such a manner that one electrode was disposed at a center and the other electrodes were disposed and equally spaced on a circle having a radius of 1.5 mm. Note that numerical values in the figure represent the dimensions of parts in units of mm. FIG. 23 is a diagram showing a resist pattern used in production of the sensor chip. FIG. 24 is a cross-sectional view showing a situation in which the resist pattern was provided on the sensor chip, indicating a cross section of the electrode 3. FIG. 25 is a plan view showing a situation in which the resist pattern was provided on the sensor chip.

INDUSTRIAL APPLICABILITY

A region in which a subject to be detected is immobilized is limited to a very small size, and a detection region of a detection means and a reaction region in which a reaction product is formed are disposed in a relative positional relationship such that the reaction product can be detected rapidly and specifically, thereby providing a sensor device which has a relatively simple structure and rapidly detects a very small amount of an analyte in a specimen, such as an immunogenic substance (e.g., a protein, a microorganism, and a virus) or a chemical substance.

As described above, the present invention is described with reference to the examples. The present invention is not so limited. The present invention can be implemented in embodiments additionally having variations, modifications, and alterations based on knowledge of those skilled in the art without departing from the spirit and scope of the present invention.

The invention claimed is:

1. A sensor device, comprising:
    a cell for containing a solution in which a redox reaction product is generated;
    at least one support means within the cell, each of said at least one support means including a fixing means to immobilize only one subject to be detected; and
    a detection means separate from the support means for detecting a current generated from said redox reaction product, wherein:
    each reaction product is generated from each of the at least one subject to be detected and the at least one subject is detected by generation of said each reaction product in a corresponding reaction region;
    one or more reaction regions are formed, each reaction region having a constant concentration of each corresponding reaction product, and each reaction region being formed by diffusion of each reaction product through the solution;
    the at least one subject to be detected is immobilized in at least one region, each region having a radius of 50 μm to 100 μm;
    each reaction region and each corresponding region in which each subject is immobilized have substantially the same size, and each reaction region and a corresponding detection region are arranged in a relative positional relationship, such that said each reaction region and said each corresponding detection region overlap substantially significantly;
    the detection means comprises one or more electrodes, each electrode corresponding to each of the one or more reaction regions in a one-to-one relationship, and each electrode corresponding to each fixing means in a one-to-one relationship; and
    for the case of more than one electrode and corresponding more than one reaction region, the more than one reaction regions are separately formed by different reaction products.

2. A sensor device according to claim 1, wherein the detection means generates the detection region, and the detection region includes the reaction region.

3. A sensor device according to claim 1, wherein the detection means generates the detection region, and the detection region overlaps the reaction region.

4. A sensor device according to claim 1, wherein the detection means generates the detection region, and the detection region is included in the reaction region.

5. A sensor device according to claim 1, wherein the support is a defined region on a base plate.

6. A sensor device according to claim 1, wherein the support is a particulate.

7. A sensor device according to claim 1, wherein the support is a rod-shaped member.

8. A sensor device according to claim 1, wherein each electrode generates an electrical signal corresponding to the amount of each reaction product.

9. A sensor device according to claim 1, wherein the subject to be detected is an enzyme, and the reaction product is an enzyme reaction product.

10. A sensor device according to claim 1, wherein the subject to be detected is an antibody or an enzyme linked to a peptide.

11. A sensor device according to claim 10, wherein the subject to be detected is immobilized by an antigen.

12. A sensor device according to claim 10, wherein the subject to be detected is immobilized by an antigen-antibody complex.

13. A sensor device according to claim 1, wherein the subject to be detected is an enzyme linked to a first antibody linked to an antigen, and is immobilized by a second antibody.

14. A sensor device according to claim 1, wherein each of the one or more electrodes has a diameter of 1 mm or less.

15. A sensor device according to claim 1, wherein each of the one or more electrodes surrounds each of the at least one region on which each of the at least one subject to be detected is immobilized.

16. A sensor device according to claim 1, wherein the support is a material selected from the group consisting of glass, ceramics, noble metals, and resins.

17. A sensor device according to claim 1, further comprising means for promoting the immobilizing of the subject to be detected.

18. A sensor device according to claim 17, wherein the promoting means is a means for stirring the solution in the cell.

19. A sensor device according to claim 17, wherein the promoting means is a means for exchanging the solution in the cell.

20. A sensor device according to claim 17, wherein the promoting means is a means for supplying the solution into the cell.

21. A sensor device according to claim 17, wherein the promoting means is a means for allowing the solution to flow through the cell.

* * * * *

UNITED STATES PATENT AND TRADEMARK OFFICE
CERTIFICATE OF CORRECTION

| | | |
|---|---|---|
| PATENT NO. | : 7,662,612 B2 | Page 1 of 1 |
| APPLICATION NO. | : 10/275783 | |
| DATED | : February 16, 2010 | |
| INVENTOR(S) | : Kazuhiro Niwa et al. | |

It is certified that error appears in the above-identified patent and that said Letters Patent is hereby corrected as shown below:

On the title page, item [73]

The assignee should be listed as:

Panasonic Ecology Systems Co., Ltd.

Signed and Sealed this
Fourteenth Day of June, 2011

David J. Kappos
*Director of the United States Patent and Trademark Office*